(12) United States Patent
Evans et al.

(10) Patent No.: US 12,023,047 B1
(45) Date of Patent: Jul. 2, 2024

(54) CANNULATED TREPHINE

(71) Applicant: University of Utah Research Foundation, Salt Lake City, UT (US)

(72) Inventors: Zackery Evans, Woods Cross, UT (US); T. Wade Fallin, Hyde Park, UT (US); Travis G. Maak, Park City, UT (US); Charles L. Saltzman, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 18/221,941

(22) Filed: Jul. 14, 2023

(51) Int. Cl.
 *A61B 17/16* (2006.01)
 *A61B 17/32* (2006.01)
(52) U.S. Cl.
 CPC ............ *A61B 17/1637* (2013.01); *A61B 2017/320056* (2013.01)
(58) Field of Classification Search
 CPC .... A61B 17/1637; A61B 2017/320056; B28D 1/041
 See application file for complete search history.

(56) References Cited

U.S. PATENT DOCUMENTS

| | | | |
|---|---|---|---|
| 1,493,240 A | 5/1924 | Bohn | |
| 2,919,692 A | 1/1960 | Wolfgang | |
| 3,893,445 A * | 7/1975 | Hofsess | A61B 10/025 604/188 |
| 4,069,824 A * | 1/1978 | Weinstock | A61B 17/1637 408/54 |
| 4,314,565 A * | 2/1982 | Lee | A61B 10/0283 600/566 |
| 4,649,918 A | 3/1987 | Pegg et al. | |
| 4,696,308 A | 9/1987 | Meller et al. | |
| 4,782,833 A | 11/1988 | Einhorn et al. | |
| 4,913,143 A | 4/1990 | Oloff et al. | |
| 5,197,967 A | 3/1993 | Wilson | |
| 5,324,300 A | 6/1994 | Elias et al. | |
| 5,330,480 A | 7/1994 | Meloul et al. | |
| 5,346,497 A | 9/1994 | Simon et al. | |
| 5,423,823 A | 6/1995 | Schmieding | |

(Continued)

FOREIGN PATENT DOCUMENTS

| | | |
|---|---|---|
| CA | 2595683 C | 3/2011 |
| WO | WO2011026164 A1 | 3/2011 |

*Primary Examiner* — Zade Coley
(74) *Attorney, Agent, or Firm* — David Meibos; Maywood IP Law

(57) ABSTRACT

A trephine may be used to form a tunnel through bone and/or cartilage. The trephine may have a trephine body with a generally tubular shape centered on a trephine body longitudinal axis, and a trephine body distal rim. The trephine may also have a drive shaft that receives torque and transmits the torque to the trephine body. The trephine body distal rim may lie substantially in a plane that is non-perpendicular to the trephine body longitudinal axis. The trephine may further have a cutting tooth extending distally from the trephine body distal rim. The cutting tooth may have a first distal tip and a second distal tip displaced circumferentially from the first distal tip. The trephine may be advanced while rotating to form the tunnel through bone and a first, adjacent cartilage surface of a joint, without breaching a second cartilage surface on the opposite side of the joint.

19 Claims, 11 Drawing Sheets

(56) References Cited

U.S. PATENT DOCUMENTS

| | | |
|---|---|---|
| 5,556,399 A | 9/1996 | Huebner |
| 5,782,835 A | 7/1998 | Hart et al. |
| 5,928,238 A | 7/1999 | Scarborough et al. |
| 6,200,319 B1 | 3/2001 | Storer et al. |
| 6,358,253 B1 | 3/2002 | Torrie et al. |
| 6,395,011 B1 | 5/2002 | Johanson et al. |
| 6,682,535 B2 | 1/2004 | Hoogland |
| 6,857,520 B2 | 2/2005 | Salazar et al. |
| 6,884,245 B2 | 4/2005 | Spranza, III |
| 6,942,669 B2 | 9/2005 | Kurc |
| 7,537,597 B2 | 5/2009 | Salazar et al. |
| RE40,796 E | 6/2009 | O'Neill |
| 8,162,967 B1 | 4/2012 | Kaiser et al. |
| 8,221,423 B2 | 7/2012 | Gil et al. |
| 8,414,585 B2 | 4/2013 | Meneghini et al. |
| 8,663,227 B2 | 3/2014 | To |
| 8,672,941 B2 | 3/2014 | Bradica et al. |
| 8,801,716 B2 | 8/2014 | Meridew |
| 8,814,882 B2 | 8/2014 | Oostman, Jr. et al. |
| 8,845,644 B1 | 9/2014 | Verhoogen |
| 8,858,133 B2 * | 10/2014 | Beynon .................. B28D 1/041 408/1 R |
| 9,084,465 B2 | 7/2015 | Oostman, Jr. et al. |
| 9,572,686 B2 | 2/2017 | Meridew |
| 9,757,135 B1 | 9/2017 | Kelley |
| 9,782,196 B2 | 10/2017 | Bradica et al. |
| 9,901,355 B2 | 2/2018 | Bourque et al. |
| 9,925,068 B2 | 3/2018 | Bays et al. |
| 10,130,343 B2 | 11/2018 | Miller et al. |
| 10,159,470 B2 | 12/2018 | McWeeney et al. |
| 10,390,806 B2 | 8/2019 | Lee et al. |
| 10,548,693 B2 | 2/2020 | Wang |
| 10,912,573 B2 | 2/2021 | Sweitzer et al. |
| 10,973,532 B2 | 4/2021 | Miller et al. |
| 11,020,244 B2 | 6/2021 | Bays et al. |
| 11,090,032 B2 | 8/2021 | Miller et al. |
| 11,185,339 B2 * | 11/2021 | Perez ........................ A61F 2/28 |
| 11,523,834 B1 * | 12/2022 | Evans ................ A61B 17/1635 |
| 2002/0099382 A1 * | 7/2002 | Salazar .................. A61B 50/30 606/86 R |
| 2003/0199879 A1 * | 10/2003 | Spranza, III ......... A61B 10/025 606/79 |
| 2004/0030343 A1 | 2/2004 | Kurc |
| 2005/0131313 A1 | 6/2005 | Mikula et al. |
| 2007/0123892 A1 | 5/2007 | Ries et al. |
| 2007/0123909 A1 * | 5/2007 | Rupp ..................... A61B 17/92 606/104 |
| 2008/0167652 A1 | 7/2008 | Reinhard |
| 2009/0270982 A1 * | 10/2009 | Torres ................... A61F 2/0095 206/363 |
| 2009/0274996 A1 | 11/2009 | Miller |
| 2010/0094361 A1 | 4/2010 | Meneghini et al. |
| 2010/0278601 A1 * | 11/2010 | Beynon .................. B28D 1/041 408/1 R |
| 2011/0177472 A1 | 7/2011 | Lee |
| 2012/0029518 A1 * | 2/2012 | Blackwell .......... A61B 17/7055 623/17.11 |
| 2012/0045731 A1 | 2/2012 | Singh |
| 2012/0053641 A1 | 3/2012 | Meridew |
| 2012/0071714 A1 * | 3/2012 | Jansen ................... A61B 1/005 600/104 |
| 2014/0288643 A1 * | 9/2014 | Torres ..................... A61F 2/148 623/5.11 |
| 2014/0309641 A1 | 10/2014 | Bourque et al. |
| 2014/0350585 A1 | 11/2014 | Meridew |
| 2017/0120357 A1 * | 5/2017 | Trautner ................ B23D 65/00 |
| 2017/0143351 A1 | 5/2017 | Devitre et al. |
| 2018/0110531 A1 | 4/2018 | Arthurs et al. |
| 2019/0388100 A1 | 12/2019 | Perez et al. |
| 2020/0367924 A1 * | 11/2020 | Lenker ........... A61B 17/320783 |
| 2021/0282940 A1 | 9/2021 | Bays et al. |

\* cited by examiner

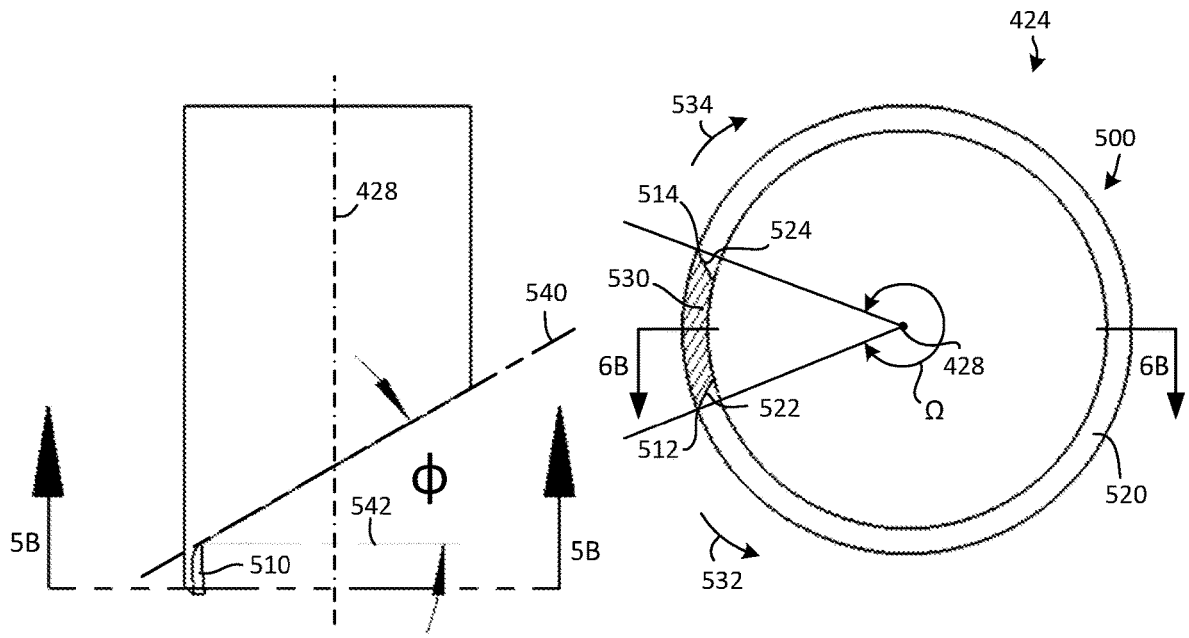
*Fig. 5A*  *Fig. 5B*
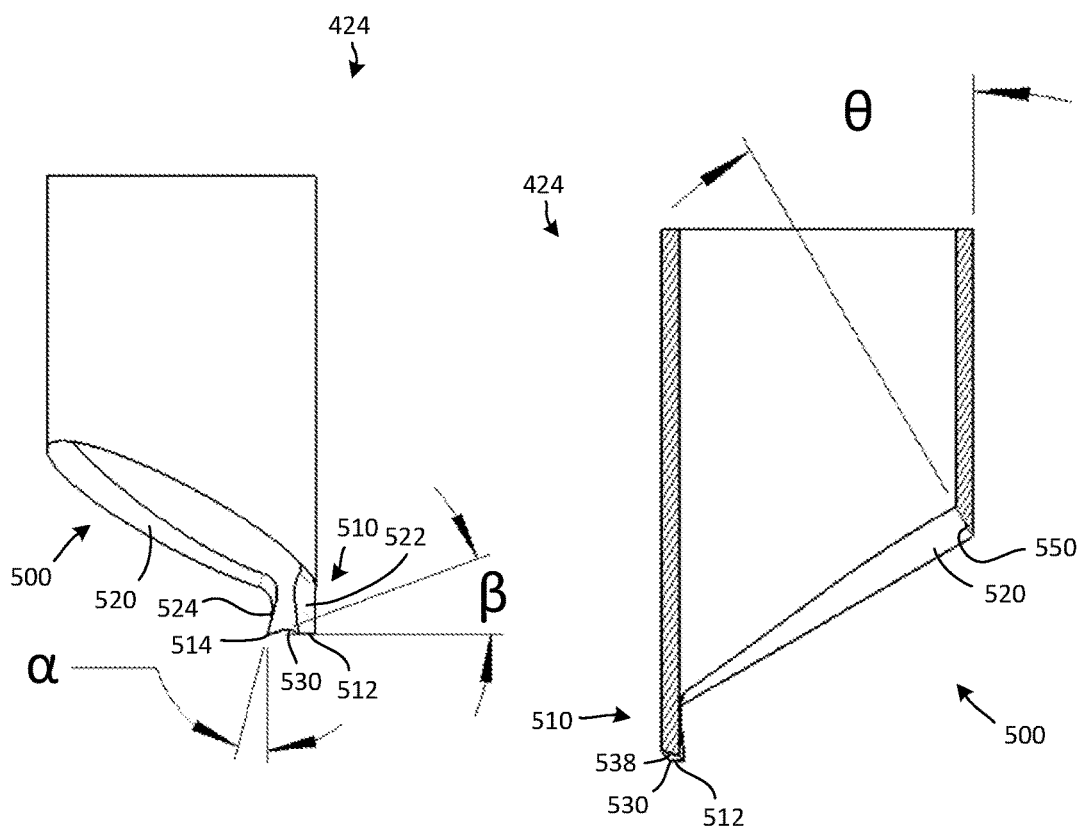
*Fig. 6A*  *Fig. 6B*

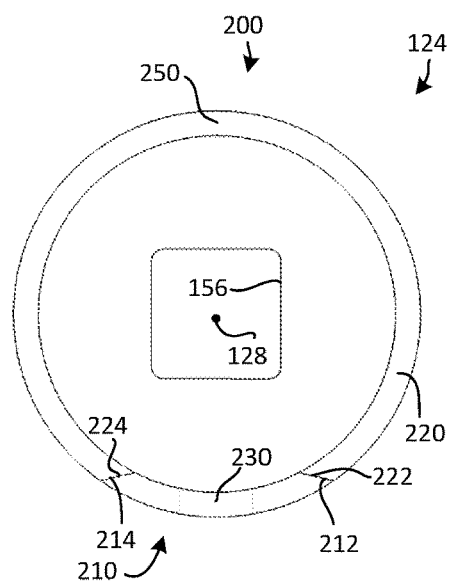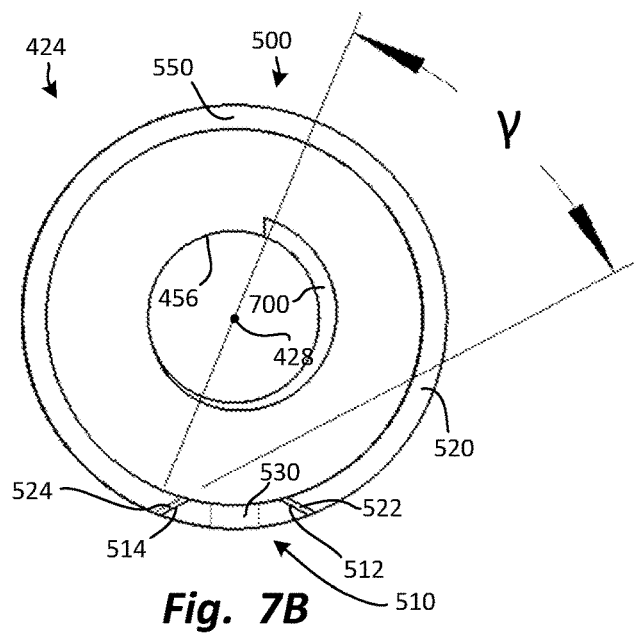
*Fig. 7A*  *Fig. 7B*
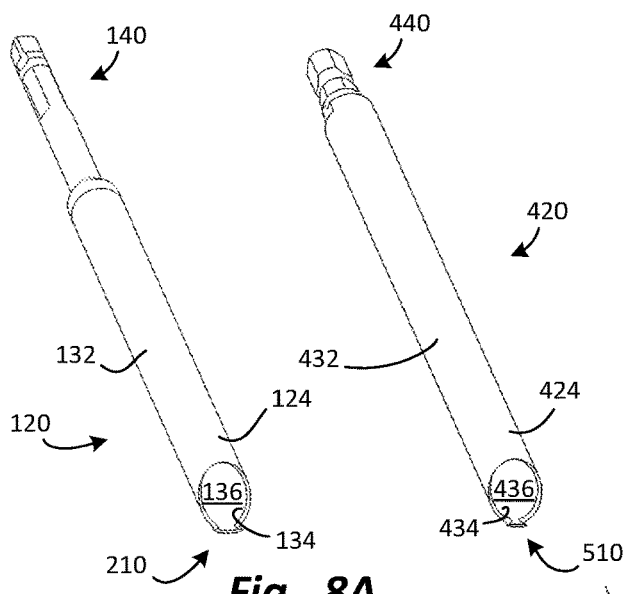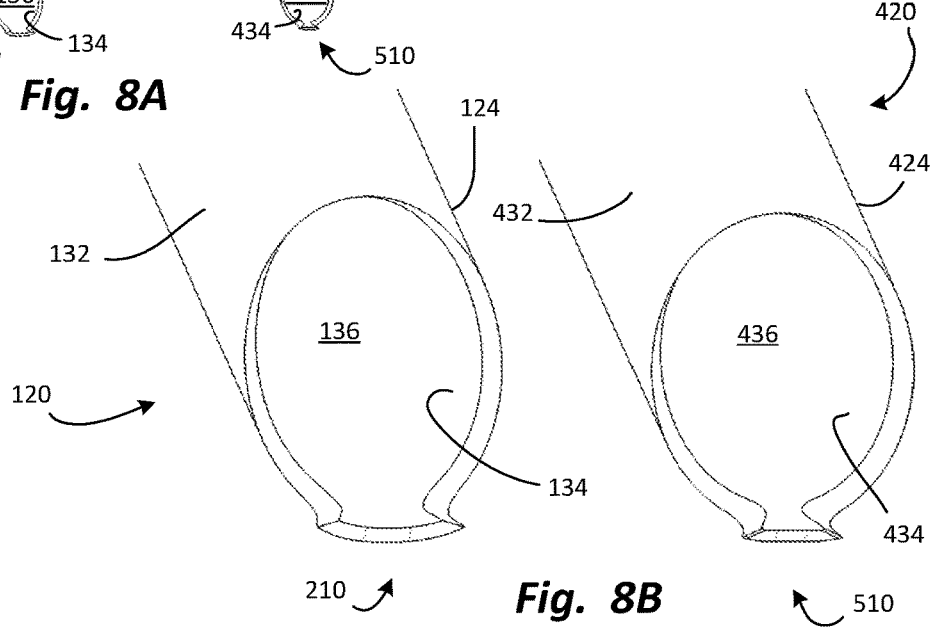
*Fig. 8A*  *Fig. 8B*

CANNULATED TREPHINE

TECHNICAL FIELD

The present disclosure relates to the field of systems, methods, and devices for bone and cartilage tunnel creation and bone and cartilage harvesting.

BACKGROUND

Tools for forming bone and cartilage tunnels and for harvesting bone and cartilage from the formed tunnels are known in the art. However, there is not a single tool that cuts both bone and cartilage effectively (bone and cartilage collectively referred to as tissue). Furthermore, cutting tissue with trephines known in the art generally create significant localized heating, which can have deleterious effects on cell viability of the harvested tissue and the tissue surrounding the formed tunnel. Additionally, to improve surgical accuracy and efficiency, a tool for forming tunnels and for harvesting tissue should have an effective means for guidance to a target location and for extracting the harvested tissue. Finally, there is a need for an improved trephine to form a retrograde tunnel that intersects a joint space.

SUMMARY

The present disclosure may provide a single tool that can efficiently and effectively cut both bone and cartilage. Further, the present disclosure may provide a single bone and cartilage cutting tool that has superior cutting efficiency, compared with current tools known in the art. Yet further, the present disclosure may provide a tissue cutting and harvesting tool that follows a guidewire and that has an effective mechanism for collecting and dispensing the harvested tissue. Finally, the present disclosure may provide a trephine that can be effectively and safely advanced from a starting point outside of a body joint space, through tissue and into a body joint space.

According to some embodiments, a trephine may be provided for forming a tunnel through bone and/or cartilage. The trephine may have a trephine body having a generally tubular shape centered on a trephine body longitudinal axis. The trephine body may have a trephine body proximal end and a trephine body distal end that defines a trephine body distal rim. The trephine may further have a drive shaft coupled to or configured to be coupled to the trephine body proximal end such that the drive shaft receives torque and transmits the torque to the trephine body. The trephine body distal rim may lie substantially in a plane that is non-perpendicular to the trephine body longitudinal axis.

For the trephine of any preceding paragraph, the plane may be oriented at a rim angle, relative to a second plane perpendicular to the trephine body longitudinal axis. The rim angle may be between 10° and 80°.

For the trephine of any preceding paragraph, the trephine may further include a cutting tooth extending distally from the trephine body distal rim.

For the trephine of any preceding paragraph, the cutting tooth may have a first distal tip and a first cutting face extending from the trephine body distal rim to the first distal tip. The first cutting face may be configured to act as a leading cutting face such that the trephine is adapted to cut the bone and/or cartilage while rotating clockwise.

For the trephine of any preceding paragraph, the cutting tooth may further have a second distal tip and a second cutting face extending from the trephine body distal rim to the second distal tip. The second cutting face may be configured to act as a leading cutting face such that the trephine is adapted to cut the bone and/or cartilage while rotating counterclockwise.

For the trephine of any preceding paragraph, the trephine body distal rim may not be interrupted by any protrusion other than the cutting tooth.

For the trephine of any preceding paragraph, the trephine body distal rim may have an uninterrupted portion that traverses at least 180° of a circumference of the trephine body distal rim.

For the trephine of any preceding paragraph, the trephine may further have a guide bushing with a guide bushing cannulation. The drive shaft may have a drive shaft cannulation. The drive shaft cannulation and the guide bushing cannulation may be configured to receive a guidewire such that the drive shaft and the guide bushing are rotatable about the guidewire. The guide bushing may be slidably receivable within the generally tubular shape such that the guide bushing is movable along the trephine body longitudinal axis as the trephine body forms the tunnel.

For the trephine of any preceding paragraph, the trephine may further have a pushrod with a proximal end configured to be slidably received or threaded into engagement within the drive shaft cannulation, and a distal end configured to push against the guide bushing to urge the guide bushing to move distally within the generally tubular shape.

According to some embodiments, a trephine may be provided for forming a tunnel through bone and/or cartilage. The trephine may have a trephine body having a generally tubular shape centered on a trephine body longitudinal axis. The trephine body may have a trephine body proximal end and a trephine body distal end that defines a trephine body distal rim. The trephine may further have a cutting tooth extending distally from the trephine body distal rim, and a drive shaft coupled to or configured to be coupled to the trephine body proximal end such that the drive shaft receives torque and transmits the torque to the trephine body. The trephine body distal rim may be non-perpendicular to the trephine body longitudinal axis and may not be interrupted by any protrusion other than the cutting tooth.

For the trephine of any preceding paragraph, the trephine body distal rim may lie substantially within a plane.

For the trephine of any preceding paragraph, the plane may be oriented at a rim angle, relative to a second plane perpendicular to the trephine body longitudinal axis. The rim angle may be between 10° and 80°.

For the trephine of any preceding paragraph, the trephine body distal rim may have an uninterrupted portion that traverses at least 180° of a circumference of the trephine body distal rim.

For the trephine of any preceding paragraph, the uninterrupted portion may traverse at least 270° of the circumference of the trephine body distal rim.

For the trephine of any preceding paragraph, the cutting tooth may have a first distal tip, and a first cutting face extending from the trephine body distal rim to the first distal tip. The first cutting face may be oriented at a longitudinal rake angle, relative to the trephine body longitudinal axis, that is greater than 0°.

For the trephine of any preceding paragraph, the cutting tooth may have a first distal tip, a second distal tip, a first cutting face extending from the trephine body distal rim to the first distal tip, and a second cutting face extending from the trephine body distal rim to the second distal tip. The first cutting face and the second cutting face may each be configured to act as a leading cutting face such that the trephine is adapted to cut the bone and/or cartilage while rotating either clockwise or counterclockwise.

According to some embodiments, a trephine may be provided for forming a tunnel through bone and/or cartilage. The trephine may have a trephine body having a generally tubular shape centered on a trephine body longitudinal axis. The trephine body may have a trephine body proximal end and a trephine body distal end that defines a trephine body distal rim with a proximal portion, and a distal portion extending distally of the proximal portion. The trephine may further have a cutting tooth extending distally from the distal portion. The cutting tooth may have a cutting tooth proximal end adjacent to the distal portion, and a cutting tooth distal end displaced distally from the distal portion. The trephine may further have a drive shaft coupled to or configured to be coupled to the trephine body proximal end such that the drive shaft receives torque and transmits the torque to the trephine body. The cutting tooth distal end may be wider than the cutting tooth proximal end.

For the trephine of any preceding paragraph, the trephine body distal rim may lie substantially within a plane that is non-perpendicular to the trephine body longitudinal axis.

For the trephine of any preceding paragraph, the plane may be oriented at a rim angle, relative to a second plane perpendicular to the trephine body longitudinal axis. The rim angle may be between 10° and 80°.

For the trephine of any preceding paragraph, the trephine body distal rim may have an uninterrupted portion that traverses at least 180° of a circumference of the trephine body distal rim.

For the trephine of any preceding paragraph, the cutting tooth distal end may have a first distal tip, and a second distal tip displaced circumferentially from the first distal tip. The first distal tip may be connected to the second distal tip by a distal surface having a concave shape.

For the trephine of any preceding paragraph, the cutting tooth may further have a first distal tip on the cutting tooth distal end, a second distal tip displaced circumferentially from the first distal tip on the cutting tooth distal end, a first cutting face extending from the trephine body distal rim to the first distal tip, and a second cutting face extending from the trephine body distal rim to the second distal tip. The first cutting face and the second cutting face may each be configured to act as a leading cutting face such that the trephine is adapted to cut the bone and/or cartilage while rotating either clockwise or counterclockwise.

According to some embodiments, a trephine may be provided for forming a tunnel through bone and/or cartilage. The trephine may have a trephine body having a generally tubular shape centered on a trephine body longitudinal axis. The trephine body may have a trephine body proximal end and a trephine body distal end that defines a trephine body distal rim. The trephine may further have a drive shaft coupled to or configured to be coupled to the trephine body proximal end such that the drive shaft receives torque and transmits the torque to the trephine body. The drive shaft may have a drive shaft cannulation. The trephine may further have a guide bushing with a guide bushing cannulation. The drive shaft cannulation and the guide bushing cannulation may be configured to receive a guidewire such that the drive shaft and the guide bushing are rotatable about the guidewire. The guide bushing may be receivable within the generally tubular shape such that the guide bushing is movable along the trephine body longitudinal axis as the trephine body forms the tunnel.

For the trephine of any preceding paragraph, the guide bushing may have a guide bushing outer surface. The trephine body may have a trephine body inner surface that defines a trephine body inner chamber. The guide bushing outer surface may be sized to have a light interference fit within the trephine body inner surface.

For the trephine of any preceding paragraph, the guide bushing may have a guide bushing outer surface. The trephine body may have a trephine body inner surface that defines a trephine body inner chamber. The guide bushing outer surface may be sized to have a close sliding clearance fit within the trephine body inner surface.

For the trephine of any preceding paragraph, the trephine may further have a pushrod with a proximal end configured to be slidably received within the drive shaft cannulation, and a distal end configured to push against the guide bushing to urge the guide bushing to move distally within the generally tubular shape.

For the trephine of any preceding paragraph, the pushrod may further have a pushrod distal end sized to be slidably received within the guide bushing cannulation, a pushrod intermediate portion that is too large to be received within the guide bushing cannulation, and a shoulder that joins the pushrod distal end with the pushrod intermediate portion.

For the trephine of any preceding paragraph, the trephine may further have a pushrod with a proximal end configured to be threaded into engagement with the drive shaft cannulation, and a distal end configured to push against the guide bushing to urge the guide bushing to move distally within the generally tubular shape.

According to some embodiments, a trephine may be provided for forming a tunnel through bone and/or cartilage. The trephine may have a trephine body having a generally tubular shape centered on a trephine body longitudinal axis. The trephine body may have a trephine body proximal end and a trephine body distal end that defines a trephine body distal rim. The trephine may further have a cutting tooth extending distally from the trephine body distal rim. The cutting tooth may have a first distal tip, and a first cutting face extending from the trephine body distal rim to the first distal tip. The trephine may further have a drive shaft coupled to or configured to be coupled to the trephine body proximal end such that the drive shaft receives torque and transmits the torque to the trephine body. The first cutting face may be oriented at a longitudinal rake angle, relative to the trephine body longitudinal axis, that is greater than 0°.

For the trephine of any preceding paragraph, the longitudinal rake angle may be greater than 10°.

For the trephine of any preceding paragraph, the cutting tooth may further have a second distal tip displaced circumferentially from the first cutting tip. The first distal tip may be connected to the second distal tip by a distal surface having a concave shape.

For the trephine of any preceding paragraph, the trephine body distal rim is not interrupted by any protrusion other than the cutting tooth.

For the trephine of any preceding paragraph, the trephine body distal rim lies substantially in a plane that is non-perpendicular to the trephine body longitudinal axis.

For the trephine of any preceding paragraph, the cutting tooth further has a second distal tip displaced circumferentially from the first distal tip, and a second cutting face extending from the trephine body distal rim to the second distal tip. The first cutting face and the second cutting face may each be configured to act as a leading cutting face such that the trephine is adapted to cut the bone and/or cartilage while rotating either clockwise or counterclockwise.

For the trephine of any preceding paragraph, the first cutting face may be oriented toward or away from an interior of the generally tubular shape at a radial rake angle that is greater than 0° or less than 0°, relative to a radial line passing through the trephine body longitudinal axis and the first cutting face.

For the trephine of any preceding paragraph, the cutting tooth may further have a cutting tooth proximal end adjacent to the trephine body distal rim, and a cutting tooth distal end displaced distally from the cutting tooth proximal end. The first distal tip and the second distal tip may be on the cutting tooth distal end. The cutting tooth distal end may be wider than the cutting tooth proximal end.

For the trephine of any preceding paragraph, the cutting tooth may extend from a first portion of the trephine body distal rim. The trephine body distal rim, on a second portion circumferentially opposite to the first portion, may have a rim cutting surface that is oriented toward an interior of the generally tubular shape at a bevel angle that is less than 90°, relative to the trephine body longitudinal axis.

According to some embodiments, a trephine may be provided for forming a tunnel through bone and/or cartilage. The trephine may have a trephine body having a generally tubular shape centered on a trephine body longitudinal axis. The trephine body may have a trephine body proximal end and a trephine body distal end that defines a trephine body distal rim. The trephine may further have a cutting tooth extending distally from the trephine body distal rim. The cutting tooth may have a first distal tip and a first cutting face extending from the trephine body distal rim to the first distal tip. The trephine may further have a drive shaft coupled to or configured to be coupled to the trephine body proximal end such that the drive shaft receives torque and transmits the torque to the trephine body. The first cutting face may be oriented toward or away from an interior of the generally tubular shape at a radial rake angle that is greater than 0° or less than 0°, relative to a radial line passing through the trephine body longitudinal axis and the first cutting face.

For the trephine of any preceding paragraph, the radial rake angle may be greater than 20°.

For the trephine of any preceding paragraph, the trephine body distal rim may not be interrupted by any protrusion other than the cutting tooth.

For the trephine of any preceding paragraph, the trephine body distal rim may lie substantially in a plane that is non-perpendicular to the trephine body longitudinal axis.

For the trephine of any preceding paragraph, the cutting tooth may further have a second distal tip circumferentially displaced from the first distal tip, and a second cutting face extending from the trephine body distal rim to the first distal tip. The first cutting face and the second cutting face may each be configured to act as a leading cutting face such that the trephine is adapted to cut the bone and/or cartilage while rotating either clockwise or counterclockwise. The second cutting face may be oriented toward or away from the interior or the exterior of the generally tubular shape at the radial rake angle, relative to a second radial line passing through the trephine body longitudinal axis and the second cutting face.

For the trephine of any preceding paragraph, the first cutting face may be oriented at a longitudinal rake angle, relative to the trephine body longitudinal axis, that is greater than 0°.

For the trephine of any preceding paragraph, the cutting tooth may extend from a first portion of the trephine body distal rim. The trephine body distal rim, on a second portion circumferentially opposite to the first portion, may have a rim cutting surface that is oriented toward an interior of the generally tubular shape at a bevel angle that is less than 90°, relative to the trephine body longitudinal axis.

According to some embodiments, a trephine may be provided for forming a tunnel through bone and/or cartilage. The trephine may have a trephine body having a generally tubular shape centered on a trephine body longitudinal axis. The trephine body may have a trephine body proximal end and a trephine body distal end that defines a trephine body distal rim. The trephine may further have a cutting tooth extending distally from a first portion of the trephine body distal rim, and a drive shaft coupled to or configured to be coupled to the trephine body proximal end such that the drive shaft receives torque and transmits the torque to the trephine body. The trephine body distal rim, on a second portion circumferentially opposite to the first portion, may have a rim cutting surface that is oriented toward an interior of the generally tubular shape at a bevel angle that is less than 90°, relative to the trephine body longitudinal axis.

For the trephine of any preceding paragraph, the bevel angle may be less than 60°.

For the trephine of any preceding paragraph, the bevel angle may be less than 45°.

For the trephine of any preceding paragraph, the trephine body distal rim may not be interrupted by any protrusion other than the cutting tooth.

For the trephine of any preceding paragraph, the trephine body distal rim may lie substantially in a plane that is non-perpendicular to the trephine body longitudinal axis.

For the trephine of any preceding paragraph, the cutting tooth may further have a first distal tip, a second distal tip displaced circumferentially from the first distal tip, a first cutting face extending from the trephine body distal rim to the first distal tip, and a second cutting face extending from the trephine body distal rim to the second distal tip. The first cutting face and the second cutting face may each be configured to act as a leading cutting face such that the trephine is adapted to cut the bone and/or cartilage while rotating either clockwise or counterclockwise.

For the trephine of any preceding paragraph, the first cutting face may be oriented toward or away from an interior of the generally tubular shape at a radial rake angle that is greater than 0° or less than 0°, relative to a radial line passing through the trephine body longitudinal axis and the first cutting face.

For the trephine of any preceding paragraph, the first cutting face may be oriented at a longitudinal rake angle, relative to the trephine body longitudinal axis, that is greater than 0°.

According to some embodiments, a method may be provided for forming a tunnel in bone and cartilage to a joint. The joint may have a first cartilage surface on a bone and a second cartilage surface separated from the first cartilage surface by a joint space. The method may include positioning a trephine body of a trephine in a retrograde approach relative to the joint, and while rotating the trephine body, advancing the trephine body at an advancement angle that is non-perpendicular to the first cartilage surface, through the bone toward the joint to create the tunnel through the bone. The method may further include further advancing the trephine body to the first cartilage surface to extend the tunnel through the first cartilage surface, such that the trephine body does not traverse the joint space to contact the second cartilage surface.

For the method of any preceding paragraph, the trephine body may have a generally tubular shape centered on a trephine body longitudinal axis. The trephine body may have a trephine body proximal end and a trephine body distal end that defines a trephine body distal rim. The trephine body may further have a cutting tooth extending distally from the trephine body distal rim. The trephine may further have a drive shaft coupled to or configured to be coupled to the trephine body proximal end to transmit torque to the trephine body.

For the method of any preceding paragraph, further advancing the trephine to the first cartilage surface may include alternately advancing and retracting the trephine to cause the cutting tooth to cut a full circumference through the first cartilage surface while avoiding contact of the cutting tooth with the second cartilage surface.

For the method of any preceding paragraph, while rotating the trephine, advancing the trephine at the advancement angle may include using a power tool to rotate the trephine. The method may further include, prior to further advancing the trephine to the first cartilage surface, disconnecting the power tool, and commencing manual control of an orientation of the trephine body.

For the method of any preceding paragraph, further advancing the trephine body to the first cartilage surface may include orienting the trephine body distal rim generally parallel to the first cartilage surface, and further advancing the trephine body without further rotation of the trephine body such that the trephine body distal rim remains generally parallel to the first cartilage surface.

For the method of any preceding paragraph, the cutting tooth may extend from a first portion of the trephine body distal rim. The trephine body distal rim, on a second portion circumferentially opposite to the first portion, may have a rim cutting surface that is oriented toward an interior of the generally tubular shape at a bevel angle that is less than 90°, relative to the trephine body longitudinal axis. Further advancing the trephine body may further include cutting through the first cartilage surface with the rim cutting surface.

For the method of any preceding paragraph, the trephine body distal rim may lie substantially in a plane that is oriented at a rim angle, relative to a second plane perpendicular to the trephine body longitudinal axis. The rim angle may be approximately the complementary angle of the advancement angle.

For the method of any preceding paragraph, the trephine body distal rim may not be interrupted by any protrusion other than the cutting tooth.

For the method of any preceding paragraph, the trephine may further include a guidewire configured to be slidably received in a drive shaft cannulation of the drive shaft. The method may further include, prior to rotating and advancing the trephine body, anchoring the guidewire in the bone along the advancement angle. While rotating the trephine body, advancing the trephine body at the advancement angle may include rotating the trephine body about the guidewire and advancing the trephine body along the guidewire.

For the method of any preceding paragraph, the trephine may further include a guide bushing configured to reside within a trephine body inner chamber of the trephine body. The guide bushing may have a guide bushing cannulation configured to slidably receive the guidewire. Positioning the trephine body in the retrograde approach relative to the joint may include positioning the trephine body with the guide bushing positioned within the trephine body inner chamber. While rotating the trephine body, advancing the trephine body at the advancement angle may include allowing the guide bushing to retract proximally within the trephine body inner chamber.

For the method of any preceding paragraph, the trephine may further have a pushrod. The method may further include, after retracting the trephine body, using the pushrod to urge the guide bushing to move distally to eject bone and/or cartilage fragments from a trephine body inner chamber of the trephine body.

For the method of any preceding paragraph, the method may further include, after further advancing the trephine body to the first cartilage surface to extend the tunnel through the first cartilage surface, retracting the trephine body along with bone and/or cartilage fragments within a trephine body inner chamber of the trephine body.

According to some embodiments, a method may be provided for forming a tunnel in bone and cartilage to a joint. The joint may include a first cartilage surface on a bone and a second cartilage surface separated from the first cartilage surface by a joint space. The method may include positioning a trephine in a retrograde approach relative to the joint. The trephine may have a trephine body having a generally tubular shape centered on a trephine body longitudinal axis. The trephine body may have a trephine body proximal end and a trephine body distal end that defines a trephine body distal rim that lies substantially in a plane that is non-perpendicular to the trephine body longitudinal axis. The trephine may further have a drive shaft coupled to or configured to be coupled to the trephine body proximal end to transmit torque to the trephine body. The method may further include, while rotating the trephine, advancing the trephine body at an advancement angle, non-perpendicular to the first cartilage surface, through the bone to the joint to create the tunnel through the bone and the first cartilage surface. The advancement angle may be determined such that, at one orientation of the trephine body about the trephine body longitudinal axis, the trephine body distal rim is generally parallel to the first cartilage surface.

For the method of any preceding paragraph, the plane may be oriented at a rim angle, relative to a second plane perpendicular to the trephine body longitudinal axis. The rim angle may be approximately the complementary angle of the advancement angle.

For the method of any preceding paragraph, the method may further include cutting the first cartilage surface by orienting the trephine body distal rim generally parallel to the first cartilage surface, and further advancing the trephine body without further rotation of the trephine body such that the trephine body distal rim remains generally parallel to the first cartilage surface.

For the method of any preceding paragraph, the trephine body may further have a cutting tooth extending distally from the trephine body distal rim. The trephine body distal rim may not be interrupted by any protrusion other than the cutting tooth.

For the method of any preceding paragraph, the cutting tooth may extend from a first portion of the trephine body distal rim. The trephine body distal rim, on a second portion circumferentially opposite to the first portion, may have a rim cutting surface that is oriented toward an interior of the generally tubular shape at a bevel angle that is less than 90°, relative to the trephine body longitudinal axis. Further advancing the trephine body may further include cutting through the first cartilage surface with the rim cutting surface.

For the method of any preceding paragraph, the trephine may further have a guidewire configured to be slidably received in a drive shaft cannulation of the drive shaft. The method may further include, prior to rotating and advancing the trephine body, anchoring the guidewire in the bone along the advancement angle. While rotating the trephine body, advancing the trephine body at the advancement angle may include rotating the trephine body about the guidewire and advancing the trephine body along the guidewire.

According to some embodiments, a method may be provided for forming a tunnel in bone and cartilage to a joint. The joint may have a first cartilage surface on a bone and a second cartilage surface separated from the first cartilage surface by a joint space. The method may include positioning a trephine in a retrograde approach relative to the joint. The trephine may include a guidewire and a trephine body having a generally tubular shape centered on a trephine body longitudinal axis. The trephine body may have a trephine body proximal end and a trephine body distal end that defines a trephine body distal rim. The trephine may further include a guide bushing with a guide bushing cannulation, and a drive shaft with a drive shaft cannulation. The drive shaft may be coupled to or configured to be coupled to the trephine body proximal end to transmit torque to the trephine body. The method may further include, while rotating the trephine, advancing the trephine along the guidewire through the bone to the joint to create the tunnel through the bone and the first cartilage surface. Advancing the trephine along the guidewire may include sliding the guide bushing proximally relative to the trephine as an interior of the trephine receives portions of the bone.

For the method of any preceding paragraph, the trephine may further include a pushrod. The method may further include, after retracting the trephine body, using the pushrod to urge the guide bushing to move distally to eject bone and/or cartilage fragments from a trephine body inner chamber of the trephine body.

For the method of any preceding paragraph, the pushrod may have a pushrod distal end, a pushrod intermediate portion, and a shoulder that joins the pushrod distal end with the pushrod intermediate portion. Using the pushrod to urge the guide bushing to move distally may include inserting the pushrod distal end into the guide bushing cannulation such that the shoulder abuts a guide bushing proximal end of the guide bushing, and sliding the pushrod through the drive shaft cannulation such that the shoulder urges the guide bushing to move distally.

For the method of any preceding paragraph, the pushrod may have a pushrod distal end, and a pushrod proximal end configured to be threaded into engagement with the drive shaft cannulation. Using the pushrod to urge the guide bushing to move distally may include positioning the pushrod distal end to abut a guide bushing proximal end of the guide bushing, and rotating the pushrod proximal end within the drive shaft cannulation such that the pushrod distal end urges the guide bushing to move distally.

These and other features and advantages of the present disclosure will become more fully apparent from the following description and appended claims or may be learned by the practice of the devices, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which:

FIG. 5A is a side view of the trephine body distal end at a second rotational position relative to the trephine body longitudinal axis.

FIG. 5B is a section view of the trephine body, along the corresponding lines shown in FIG. 5A.

FIG. 6A is a side view of the trephine body distal end at a third rotational position relative to the trephine body longitudinal axis.

FIG. 6B is a section view of the trephine body distal end, along the corresponding lines shown in FIG. 5B.

FIG. 7A is an end view of the trephine body distal end shown in FIG. 3A.

FIG. 7B is an end view of the trephine body distal end shown in FIG. 3B.

FIG. 8A is a perspective view of the trephine body and the drive shaft of FIG. 3A (left) and the trephine body and the drive shaft of FIG. 3B (right).

FIG. 8B is an enlarged, perspective view of the trephine body distal ends of FIGS. 3A and 3B, respectively, shown in FIG. 8A.

Figure 1:
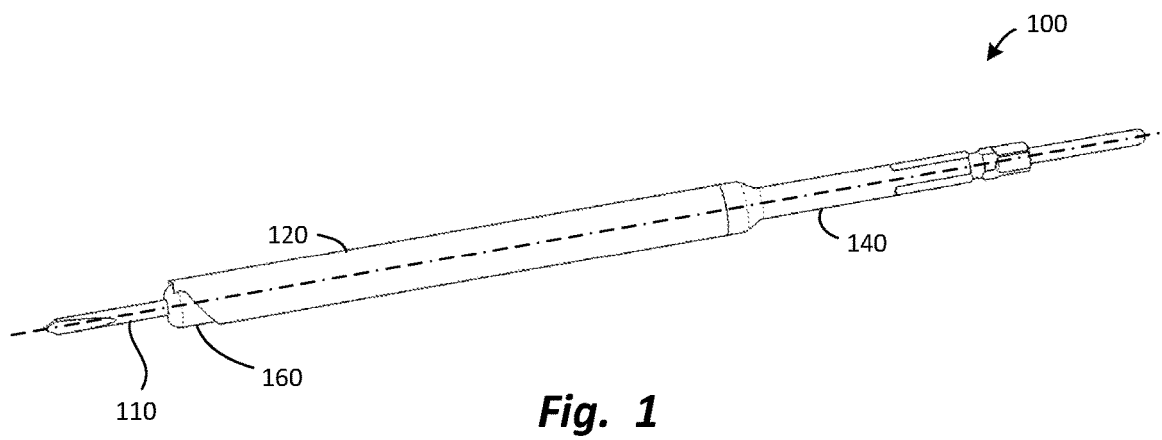
FIG. 1 is a perspective view of a trephine in an assembled state, according to one embodiment.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the implants, systems, and methods, as represented in the drawings, is not intended to limit the scope of the present disclosure, but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter.

For purposes of interpreting this specification, the following definitions will apply. In the event that any definition set forth below conflicts with any document incorporated herein by reference, the definition set forth below shall control.

Bone and cartilage are referred to, collectively, as tissue. Proximal means closer to a user, distal means farther away from a user. For example, the handle of a screwdriver is on a proximal end, and the drive tip of a screwdriver is on a distal end. Parallel direction means a direction that is parallel to an object such as a trephine body longitudinal axis. Circumferential direction means in a direction around the circumference of an object, for example, along a circumference encircling a trephine body longitudinal axis. The words "generally" and "substantially," in reference to an angular or linear measurement or comparison, mean within 10% of the angular or linear amount to which they refer.

Figure 2:
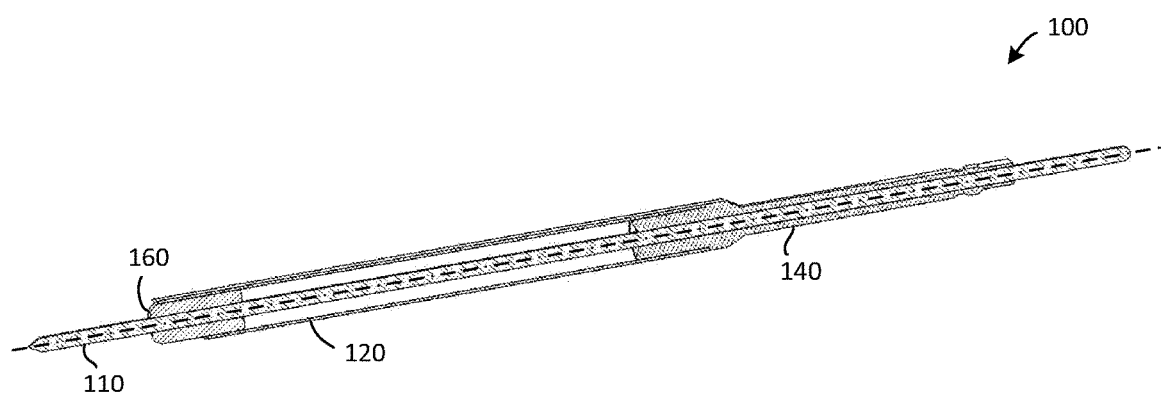
FIG. 2 is a perspective section view of the trephine of FIG. 1.
Figure 3A:
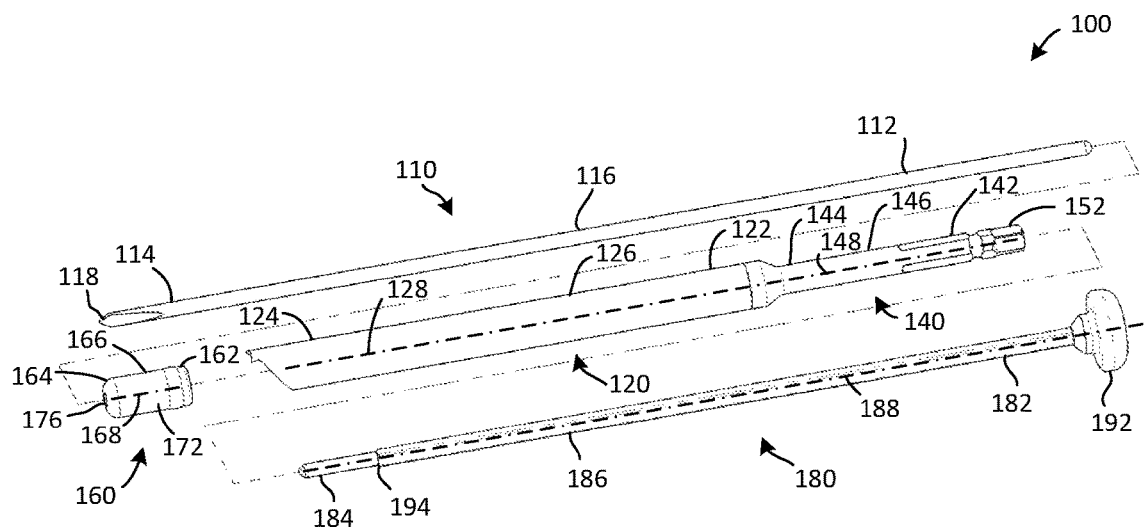
FIG. 3A is an exploded perspective view of the trephine of FIG. 1

FIG. 1 is a perspective view of a trephine 100 in an assembled state, according to one embodiment. FIG. 2 is a perspective section view of the trephine 100 of FIG. 1. FIG. 3A is an exploded perspective view of the trephine 100 of FIG. 1, which may include a guidewire 110, a trephine body 120, a drive shaft 140, a guide bushing 160, and a pushrod 180. In this disclosure, a "trephine" is a cutting instrument that cuts through tissue, such as bone and cartilage, primarily through repetitive rotation such that the tissue is received within an interior of the cutting instrument. A trephine may have drive shaft 140 that is configured to be connected to a power tool, to receive input torque or rotation from a surgical power tool, and to transmit that torque to trephine body 120.

The guidewire 110 may have a proximal end 112, a distal end 114, and an intermediate portion 116. The distal end 114 may have a sharpened tip 118 configured to pierce bone and/or cartilage. The guidewire 110 may be easily anchored with accuracy in bone so that the surgeon can tightly control the angle at which the trephine 100 enters the bone and/or cartilage.

The trephine body 120 may have a trephine body proximal end 122, a trephine body distal end 124, a trephine body intermediate portion 126, and a trephine body longitudinal axis 128 extending from the trephine body proximal end 122 to the trephine body distal end 124. The trephine body may have a generally tubular shape that is bounded by a trephine body outer surface 132 and a trephine body inner surface 134. The trephine body inner surface 134 may bound and define a trephine body inner chamber 136.

A "generally tubular shape" is a shape that has a cylindrical interior wall and a cylindrical exterior wall. However, some slight deviations from cylindricity may exist, such as surface features, texturing, etching, or aberrations inherent in the manufacturing methods used to make the generally tubular shape. A "generally tubular shape" need not have cylindrical interior and exterior walls along its entire length; rather, it may have a cap at one or both ends. A "generally tubular shape" may have a slight interior and/or exterior taper.

The drive shaft 140 may have a drive shaft proximal end 142, a drive shaft distal end 144, a drive shaft intermediate portion 146, and a drive shaft longitudinal axis 148 extending from the drive shaft proximal end 142 to the drive shaft distal end 144. The drive shaft 140 may have a drive shaft cannulation 156 extending along the drive shaft longitudinal axis 148. The drive shaft distal end 144 may be adapted to be connected to the trephine body proximal end 122 such that the drive shaft longitudinal axis 148 is coaxial with the trephine body longitudinal axis 128. The drive shaft 140 may also have a drive feature 152, such as a hexagonal protrusion, that can engage other manual and/or power-driven instruments to facilitate transmission of torque to the trephine body 120 through the drive shaft 140. The drive feature 152, or the drive shaft 140 as a whole, may have a width that is smaller than that of the trephine body 120 so that the drive feature 152 can be received into a rotating driver, such as a surgical power tool, to impart torque to the drive shaft 140. This torque may be transmitted by the drive shaft 140 to the trephine body 120 to cause the trephine body 120 to cut through bone and/or cartilage.

The connection between the drive shaft distal end 144 and trephine body proximal end 122 may be permanent or the connection may be a releasable connection. Any connection mechanism may be used, including but limited to mechanical fastening devices, chemical bonds, adhesive bonds, welds, and/or the like. Alternatively, the trephine body and the drive shaft can be made unitary, e.g., as a single piece.

The guide bushing 160 may have a guide bushing proximal end 162, guide bushing distal end 164, a guide bushing intermediate portion 166, and a guide bushing longitudinal axis 168 extending from the guide bushing proximal end 162 to the guide bushing distal end 164. The guide bushing 160 may have a guide bushing cannulation 176 extending along the guide bushing longitudinal axis 168. The guide bushing 160 may have a guide bushing outer surface 172 sized to provide either a light interference fit or a closing sliding fit with the trephine body inner surface 134.

The pushrod 180 may have a pushrod proximal end 182, a pushrod distal end 184, a pushrod intermediate portion 186, and a pushrod longitudinal axis 188 extending from the pushrod proximal end 182 to the pushrod distal end 184. The pushrod may have a handle 192 at the pushrod proximal end 182, and a shoulder 194 near the pushrod distal end 184. The pushrod intermediate portion 186 may be substantially smooth to enable the pushrod 180 to slide freely through the drive shaft cannulation 156.

The pushrod distal end 184 (e.g., the portion of the pushrod 180 distal to the shoulder 194) may have a smaller diameter than the pushrod intermediate portion 186 (e.g., the portion of the pushrod 180 between the shoulder 194 and the pushrod proximal end 182). Thus, the pushrod distal end 184 may be insertable into the guide bushing cannulation 176, but the pushrod intermediate portion 186 may be too large to fit into the guide bushing cannulation 176 such that the shoulder 194 abuts and pushes on the guide bushing proximal end 162 in response to distal pressure on the handle 192. This pressure may cause the guide bushing 160 to move distally to push any collected bone and/or cartilage out of the trephine body inner chamber 136.

The light interference fit between the guide bushing outer surface 172 and the trephine body inner surface 134 may cause the guide bushing 160 to remain in place (for example, near the trephine body distal end 124) until pressed proximally by bone and/or cartilage entering the trephine body inner chamber 136. Then, the guide bushing 160 may move proximally as the bone and/or cartilage collects within the trephine body inner chamber 136, until the guide bushing 160 is moved distally again by the pushrod 180.

Figure 3B:
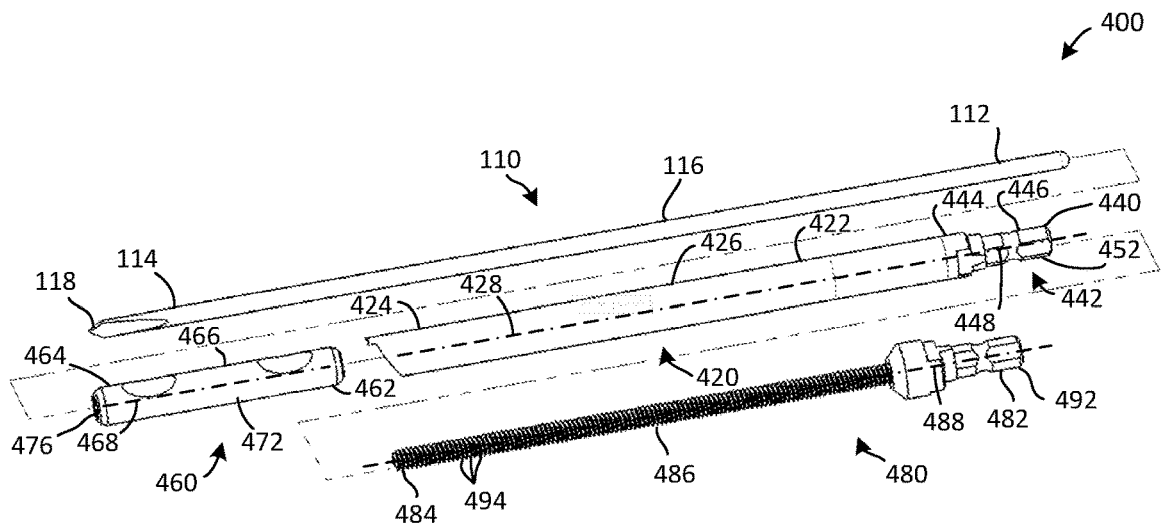
FIG. 3B is an exploded perspective view of a trephine according to one alternative embodiment.

FIG. 3B is an exploded perspective view of a trephine 400 according to one alternative embodiment, including a guidewire 110, a trephine body 420, a drive shaft 440, a guide bushing 460, and a pushrod 480. The guidewire 110 may be configured substantially as described in connection with the trephine 100 of FIG. 1. The trephine body 420, a drive shaft 440, a guide bushing 460, and a pushrod 480 may be similar in cooperation and function, with some differences.

For example, the trephine body 420 may be shaped similarly to the trephine body 120, except that the trephine body 420 may be somewhat longer, and therefore better suited to creation of longer bone/cartilage tunnels. Like the trephine body 120, the trephine body 420 may have a trephine body proximal end 422, a trephine body distal end 424, a trephine body intermediate portion 426, a trephine body longitudinal axis 428, a trephine body outer surface 432, a trephine body inner surface 434, and a trephine body inner chamber 436.

The drive shaft 440 may be shorter than the drive shaft 140, and may be designed to interface with the pushrod 480. Like the drive shaft 140, the drive shaft 440 may have a drive shaft proximal end 442, a drive shaft distal end 444, a drive shaft intermediate portion 446, a drive shaft longitudinal axis 448, a drive feature 452, and a drive shaft cannulation 456. The drive shaft cannulation 456 may be threaded to interface with the pushrod 480 such that the pushrod 480 can be rotated to advance it through the drive shaft cannulation 456, pushing on the guide bushing 460 to urge the guide bushing 460 to move distally.

The guide bushing 460 may provide a close sliding fit with the trephine body inner surface 434. The close sliding fit may be functionally similar to the light interference fit between the guide bushing 160 and the trephine body 120, but may enable the guide bushing 460 to slide relatively more easily within the trephine body inner surface 434. The guide bushing 460 may also be longer than the guide bushing 160. Like the guide bushing 160, the guide bushing 460 may have a guide bushing proximal end 462, a guide bushing distal end 464, a guide bushing intermediate portion 466, a guide bushing longitudinal axis 468, and a guide bushing cannulation 476.

The pushrod 480 of FIG. 3B may be configured differently from the pushrod 180, in that the pushrod 480 may be designed for threaded engagement with and advancement relative to the drive shaft 440. Thus, the pushrod 480 may have a pushrod proximal end 482, a pushrod distal end 484, a pushrod intermediate portion 486, and a pushrod longitudinal axis 488.

However, in place of the handle 192, the pushrod 480 may have a drive feature 492 at the pushrod proximal end 482 to facilitate rotation of the pushrod 480 by hand (for example, with a crank) or via a power tool. In place of the shoulder 194, the pushrod 480 may have threading 494 along the pushrod distal end 484 and the pushrod intermediate portion 486 that is configured to engage internal threading (not shown) within the drive shaft cannulation 456. Thus, the pushrod 480 may be advanced distally, or retracted proximally, via rotation relative to the trephine body 420 and the drive shaft 440.

The close sliding fit between the guide bushing outer surface 472 and the trephine body inner surface 434 may cause the guide bushing 460 to remain in place (for example, near the trephine body distal end 424) until pressed proximally by bone and/or cartilage entering the trephine body inner chamber 436. Then, the guide bushing 460 may move proximally as the bone and/or cartilage collects within the trephine body inner chamber 436, until the guide bushing 460 is moved distally again via rotation of the pushrod 480.

Figure 4:
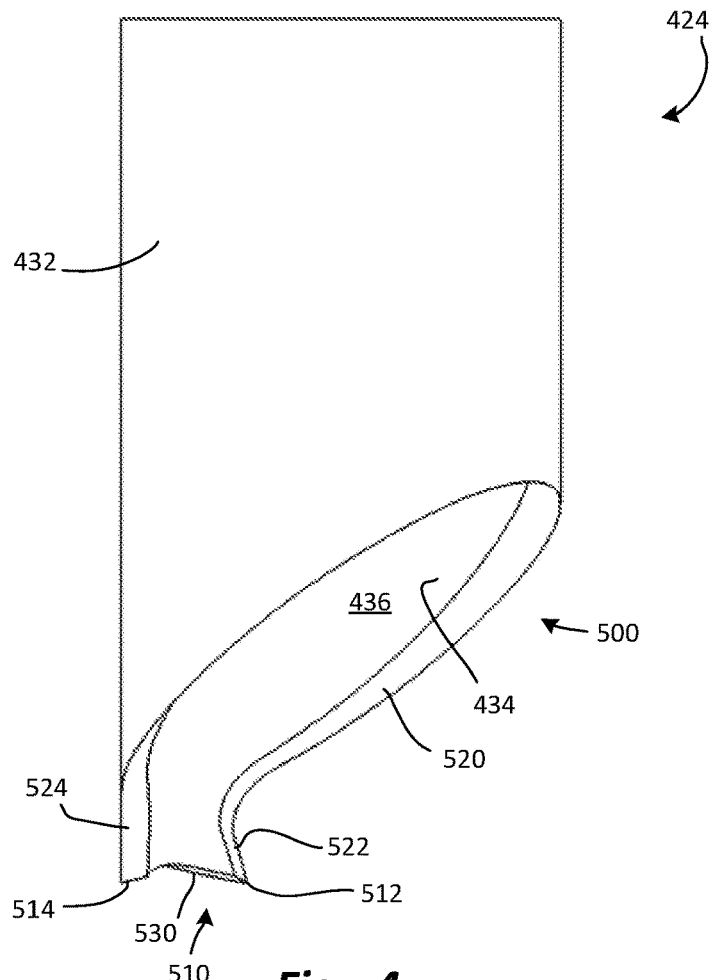
FIG. 4 is a side view of the trephine body distal end of the trephine body of FIG. 3A, at a first rotational position relative to the trephine body longitudinal axis.

FIG. 4 is a side view of the trephine body distal end 424 of the trephine body 420 of FIG. 3A, at a first rotational position relative to the trephine body longitudinal axis 428. FIG. 5A is a side view of the trephine body distal end 424 at a second rotational position relative to the trephine body longitudinal axis 428. FIG. 5B is a section view of the trephine body 420, along the corresponding lines shown in FIG. 5A. FIG. 6A is a side view of the trephine body distal end 424 at a third rotational position relative to the trephine body longitudinal axis 428. FIG. 6B is a section view of the trephine body distal end 424, along the corresponding lines shown in FIG. 5B.

FIG. 7A is an end view of the trephine body distal end 124 shown in FIG. 3A. FIG. 7B is an end view of the trephine body distal end 424 shown in FIG. 3B. FIG. 8A is a perspective view of the trephine body 120 and the drive shaft 140 of FIG. 3A (left) and the trephine body 420 and the drive shaft 440 of FIG. 3B (right). FIG. 8B is an enlarged, perspective view of the trephine body distal end 124 and the trephine body distal end 424 of the trephine body 120 and the trephine body 420, respectively, shown in FIG. 8A.

With reference to FIG. 5A, the trephine body distal end 424 of the trephine body 420 may have a trephine body distal rim 500. The trephine body distal rim 500 may cut bone and/or cartilage to form the tunnel. Additionally or alternatively, the trephine body distal rim 500 may direct fragments of removed bone and/or cartilage into the trephine body inner chamber 436 of the trephine body 420 to remove them from the cutting area and/or retain them for subsequent therapeutic use. According to some examples, harvested bone and/or cartilage may be retained and grafted into a new location, or even back in the tunnel from which they are removed. If desired, only healthy bone and/or cartilage may be retained and used so that only healthy tissue is inserted back into the tunnel.

A cutting tooth 510 may extend distally from the trephine body distal rim 500. More specifically, the trephine body distal rim 500 may have a proximal portion and a distal portion (for example, the portions of the trephine body distal rim 500 on the right and left sides of the trephine body longitudinal axis 428, respectively). The cutting tooth 510 may be integrally formed with the trephine body distal rim 500, or may be formed separately and attached thereto by any method known in the art, including but not limited to mechanical fastening, chemical bonding, adhesive bonding, welding, and the like. As shown, only a single cutting tooth (e.g., the cutting tooth 510) may be present; the cutting tooth 510 may be configured to cut the bone and/or cartilage independently of any other teeth or other cutting implements. Thus, in the embodiment shown, no other cutting feature besides the cutting tooth 510 may extend distally beyond the trephine body distal rim 500.

Thus, the trephine body distal rim 500 may have an uninterrupted portion 520 that traverses an angle $\Omega$ of at least 180° of the circumference of the trephine body distal rim 500. More specifically, the angle $\Omega$ may be at least 270° of the circumference of the trephine body distal rim 500. Yet more specifically, the angle $\Omega$ may be at least 300° of the circumference of the trephine body distal rim 500. Still more specifically, the angle $\Omega$ may be at least 315° of the circumference of the trephine body distal rim 500. This is more clearly shown in FIG. 5B.

With reference also to FIG. 8A, the cutting tooth 510 may have a first distal tip 512 shown on the right and a second distal tip 514 shown on the left. The first distal tip 512 may connect to the trephine body distal rim 500 via a first cutting face 522, and the second distal tip 514 may connect to the trephine body distal rim 500 via a second cutting face 524. The first distal tip 512 may be connected to the second distal tip 514 by a distal surface 530. The distal surface 530 may have a concave shape such that the first distal tip 512 and/or the second distal tip 514 are acutely angled. The first cutting face 522 and/or the second cutting face 524 may be tapered such that they approach each other along the proximal direction to further accentuate the acute angulation of the first distal tip 512 and/or the second distal tip 514. In other words, the first cutting face 522 and/or the second cutting face 524 may be angled to face slightly toward the trephine body distal rim 500. This angulation may cause the cutting tooth 510 to be wider at its distal end than at its proximal end. The angulation of the first cutting face 522 and/or the second cutting face 524 may cause the first cutting face 522 and/or the second cutting face 524 to have a positive longitudinal rake angle under clockwise rotation and/or counterclockwise rotation, respectively.

The first distal tip 512 and the second distal tip 514 may be spaced apart in a circumferential direction such that the first distal tip 512 and the first cutting face 522 are adapted to efficiently cut in a clockwise direction 532, and the second distal tip 514 and the second cutting face 524 are adapted to efficiently cut in a counterclockwise direction 534. Clockwise rotation is rotation about the trephine body longitudinal axis 128, as viewed from the trephine body proximal end 122 looking toward the trephine body distal end 124.

With reference to FIG. 6A, the second cutting face 524 may approach the second distal tip 514 at a longitudinal rake angle $\alpha$, relative to the trephine body longitudinal axis 128. The longitudinal rake angle $\alpha$ may cause the second cutting face 524 to be inclined from a distal left point to a proximal right point to further facilitate efficient cutting in the counterclockwise direction 534. Notably, the "positive" longitudinal rake angle $\alpha$ means that distal end of the second cutting face 524 encounters bone and/or cartilage to be cut before the proximal end of the second cutting face 524. This may help pull material away from where cutting is occurring, accelerating penetration of the bone and/or cartilage. The first cutting face may have the same longitudinal rake angle $\alpha$, relative to the trephine body longitudinal axis 128 to further facilitate efficient cutting in the clockwise direction 532.

In some embodiments, the longitudinal rake angle $\alpha$ may be within the range of 0° to 60°. More precisely, in some embodiments, the longitudinal rake angle $\alpha$ may be within the range of 5° to 50°. Yet more precisely, in some embodiments, the longitudinal rake angle $\alpha$ may be within the range of 10° to 40°. Still more precisely, in some embodiments, the longitudinal rake angle $\alpha$ may be within the range of 15° to 30°. Even more precisely, in some embodiments, the longitudinal rake angle $\alpha$ may be within the range of 20° to 27°. Still further, in some embodiments, the longitudinal rake angle $\alpha$ may be about 25°.

With reference to FIG. 7A, each of the first cutting face 522 and the second cutting face 524 may be angled toward the trephine body inner chamber 436 such that they effectively remove bone and/or cartilage to form the tunnel, and so that they direct removed bone and/or cartilage into the trephine body inner chamber 436. More specifically, the first cutting face 522 and the second cutting face 524 may each be oriented at a radial rake angle $\gamma$, as shown. The radial rake angle $\gamma$ may be the angle of the first cutting face 522 and/or the second cutting face 524 relative to a radial line passing from the trephine body longitudinal axis 428, passing through the first cutting face 522 or the second cutting face 524, respectively, as shown in FIG. 7B.

In some embodiments, the radial rake angle $\gamma$ may be within the range of 0° to 80°. More precisely, in some embodiments, the radial rake angle $\gamma$ may be within the range of 10° to 70°. Yet more precisely, in some embodiments, the radial rake angle $\gamma$ may be within the range of 20° to 60°. Still more precisely, in some embodiments, the radial rake angle $\gamma$ may be within the range of 30° to 50°. Even more precisely, in some embodiments, the radial rake angle $\gamma$ may be within the range of 35° to 45°. Still further, in some embodiments, the radial rake angle $\gamma$ may be about 40°. Optionally, the radial rake angle $\gamma$ may be the same for the first cutting face 522 and the second cutting face 524 to facilitate efficient cutting in the clockwise direction 532 and the counterclockwise direction 534, respectively.

With reference to FIG. 4 and FIG. 6A, the distal surface 530 may have a concave shape such that it is angled at a relief angle $\beta$ as it approaches each of the first distal tip 512 and the second distal tip 514. The relief angle $\beta$ may be the angle that exists between the portion of the distal surface 530 adjacent to the first distal tip 512 and the second distal tip 514, and a plane that is perpendicular to the trephine body longitudinal axis 428 of the trephine body 420 (for example, a plane parallel to the plane 542 of FIG. 5A). The relief angle $\beta$ adjacent to the second distal tip 524 may be most apparent when viewed from perpendicular to the portion of the distal surface 530 adjacent to the second distal tip 514, as in FIG. 6A. The relief angle $\beta$ may cause the distal surface 530 to extend circumferentially and proximally, away from the first distal tip 512 and the second distal tip 514, respectively, to reduce "drag" or friction of the cutting tooth 510 as it rotates circumferentially in the bone and/or cartilage that is being cut.

In some embodiments, the relief angle β may be within the range of 0° to 60°. More precisely, in some embodiments, the relief angle β may be within the range of 5° to 40°. Yet more precisely, in some embodiments, the relief angle β may be within the range of 10° to 30°. Still more precisely, in some embodiments, the relief angle β may be within the range of 12° to 25°. Even more precisely, in some embodiments, the relief angle β may be within the range of 15° to 20°. Still further, in some embodiments, the relief angle β may be about 18°.

Together, the relief angle β, the radial rake angle γ and the longitudinal rake angle α may define cutting characteristics of the first distal tip 512, the first cutting face 522, the second distal tip 514, and the second cutting face 524. More specifically, the radial rake angle γ and the longitudinal rake angle α may define a single compound angle plane for each of the first cutting face 522 and the second cutting face 524.

With V reference to FIG. 5A, FIG. 6A and FIG. 6B, the trephine body distal rim 500 may extend in the circumferential direction and may lie substantially in a plane 540. A feature that "lies substantially in" a plane is a feature for which all points are in the plane. Some departures from the plane may exist, for example, where the feature has surface features, manufacturing defects, or very minor protuberances or recesses that do not result in a significant departure from the plane.

The plane 540 may be oriented at a rim angle φ such that the plane 540 is non-perpendicular to the trephine body longitudinal axis 428, and is thus nonparallel to a plane 542 perpendicular to the trephine body longitudinal axis 428. The rim angle φ is the angle between the plane 540 and the plane 542.

The rim angle φ may be generally between 10° and 80° relative to the trephine body longitudinal axis 428, and more specifically between 15° and 65° relative to the trephine body longitudinal axis 428. Yet more specifically, the rim angle φ may be between 20° and 50° relative to the trephine body longitudinal axis 428, and more specifically, between 30° and 40° relative to the trephine body longitudinal axis 428.

In some embodiments, the trephine body 420 may be provided in a variety of dimensions, with varying rim angles φ to accommodate different angles of the tunnel relative to the cartilage surface at which the tunnel is to terminate. For example, a set of trephine bodies (not shown) may have trephine body distal rims with rim angles φ of 10°, 20°, 30°, 40°, and 50° to facilitate formation of tunnels that are angled at 10°, 20°, 30°, 40°, and 50°, respectively, relative to a vector normal to the cartilage surface at which the tunnel is to terminate.

As shown in FIG. 6A and FIG. 6B, the trephine body distal rim 500 may have a rim cutting surface 550 on the uninterrupted portion 520. The rim cutting surface 550 may be adapted for cutting in a direction that is parallel to the trephine body longitudinal axis 428. The rim cutting surface 550 may have a bevel angle θ as shown in FIG. 6B. As the trephine body 420 cuts and traverses deeper into the tissue, the bevel angle θ may provide for efficient cutting in a direction that is parallel to the trephine body longitudinal axis 428. Thus, the first cutting face 522, the second cutting face 524, and/or the distal surface 530 may generally cut tissue in response to rotation of the trephine body longitudinal axis 428, while the rim cutting surface 550 cuts the tissue in response to axial advancement of the trephine body longitudinal axis 428 into the tissue.

The bevel angle θ may provide for efficient cutting in response to this axial motion, and/or efficient direction of bone and/or cartilage fragments into the trephine body inner chamber 436 of the trephine body 420. Notably, the bevel angle θ may be the angle of the rim cutting surface 550 of the trephine body distal rim 500 at a position diametrically opposed to that of the cutting tooth 510. As shown in FIG. 6B, the rim cutting surface 550 may have a variable angle, relative to the trephine body longitudinal axis 428, with the bevel angle θ as the minimum relative angle, and progressively larger angles (leading the rim cutting surface 550 to become more nearly perpendicular to the trephine body longitudinal axis 428) as the rim cutting surface 550 approaches the cutting tooth 510. Adjacent to the cutting tooth 510, the rim cutting surface 550 may be perpendicular, or nearly perpendicular, to the trephine body longitudinal axis 428.

In some embodiments, the bevel angle θ may be within the range of 10° to 80°. More precisely, in some embodiments, the bevel angle θ may be within the range of 15° to 70°. Yet more precisely, in some embodiments, the bevel angle θ may be within the range of 20° to 60°. Still more precisely, in some embodiments, the bevel angle θ may be within the range of 25° to 50°. Even more precisely, in some embodiments, the bevel angle θ may be within the range of 30° to 45°. Still further, in some embodiments, the bevel angle θ may be about 35°.

FIG. 6B further depicts the concave shape of the distal surface 530. The section view of FIG. 6B may be taken through the center of the distal surface 530, which may be the proximal-most portion of the distal surface 530. Thus, the half of the distal surface 530 leading from the cutting plane to the first distal tip 512 is shown. The center of the distal surface 530 may have an edge 538 oriented outward, i.e., away from the trephine body longitudinal axis 428, as shown.

The radial rake angle γ and/or the bevel angle θ may all define leading edges on the trephine body outer surface 432 and trailing edges on the trephine body inner surface 434, such that the first cutting face 522, second cutting face 524, and rim cutting surface 550 are oriented toward the trephine body inner surface 434. In one alternative embodiment (not shown), all leading edges can be on the trephine body inner surface 434, and all trailing edges can be on the trephine body outer surface 432, such that the first cutting face 522, second cutting face 524, and rim cutting surface 550 are oriented toward the trephine body outer surface 432. In another alternative embodiment (not shown), leading and trailing edges of the radial rake angle γ and/or the bevel angle θ can be on different combinations of the trephine body inner surface 434 and the trephine body outer surface 432.

FIG. 7A shows the drive shaft cannulation 156 of the drive shaft 140 of the trephine 100 in greater detail. As shown, the drive shaft cannulation 156 may have a non-circular shape centered on the trephine body longitudinal axis 428. The drive shaft cannulation 156 may enable the pushrod intermediate portion 186 of the pushrod 180 to slide therethrough without rotation.

By contrast, FIG. 7B shows the drive shaft cannulation 456 of the drive shaft 440 of the trephine 400. The drive shaft cannulation 456 may have an internal thread 700 that extends through the drive shaft 440 of the trephine 400 shown in FIG. 3B along the trephine body longitudinal axis 428. The drive shaft cannulation 456 may receive the pushrod intermediate portion 486 of the pushrod 480 in threaded engagement, permitting the pushrod 480 to be advanced and/or retracted, relative to the drive shaft 440, via relative rotation between the pushrod 480 and the drive shaft 440.

FIGS. 7A, 8A, and 8B also show the trephine body distal end 124 of the trephine body 120 of the trephine 100 of FIG. 3A in greater detail. The trephine body distal end 124 may have a shape that is generally similar to that of the trephine body distal end 424. More particularly, like the trephine body distal end 424, the trephine body distal end 124 may have a trephine body distal rim 200 that extends within a plane that is non-perpendicular to the trephine body longitudinal axis 128 of the trephine body 120.

The trephine body distal end 124 may have a cutting tooth 210 extending distally from the trephine body distal rim 200. The cutting tooth 210 may have a first distal tip 212 and a second distal tip 214, with a distal surface 230 that connects the first distal tip 212 to the second distal tip 214. A first cutting face 222 may extend distally from the trephine body distal rim 200 to the first distal tip 212, and a second cutting face 224 may extend distally from the trephine body distal rim 200 to the second distal tip 214.

The first distal tip 212 and the first cutting face 222 may be used to cut in the clockwise direction 532, and the second distal tip 214 and the second cutting face 224 may be used to cut in the counterclockwise direction 534. An uninterrupted portion 220 of the trephine body distal rim 200 may extend circumferentially from the first cutting face 222 to the second cutting face 224. The uninterrupted portion 220 may define a rim cutting surface 250 as shown.

The trephine body distal end 124 of FIG. 3A may also have a radial rake angle γ, the longitudinal rake angle α, the bevel angle θ, the rim angle φ, and/or a relief angle β; these angles may optionally be as shown and described for the second cutting face 524 of FIG. 3B. However, the cutting tooth 210 may generally be wider than the cutting tooth 510, such that the sweep angle occupied by the uninterrupted portion 220 of the trephine body distal rim 200 may be less than the corresponding sweep angle occupied by the uninterrupted portion 520 of the trephine body distal rim 500.

Thus, the distal surface 230 may be longer than the distal surface 530. This may cause the longitudinal rake angle α defined by the distal surface 230 to be less than the longitudinal rake angle α defined by the distal surface 530, as distal surface 230 may be concave with a larger radius than that of the distal surface 530. The effect of this may be to cause the cutting tooth 210 to cut somewhat less aggressively than the cutting tooth 510. As used herein, the word "concave" includes concavely curved surfaces as well as flat, faceted surfaces that are arranged together to provide a shape that approximates that of a concavely curved surface.

In some embodiments, the guide bushing 160 or the guide bushing 460 may be replaced with alternatives that provide greater control over the level of resistance to sliding motion between the guide bushing 160 and the trephine body inner surface 134, or between the guide bushing 460 and the trephine body inner surface 434. Some examples will be shown and described in connection with FIG. 9A, FIG. 9B, and FIG. 9C.

Figure 9A:
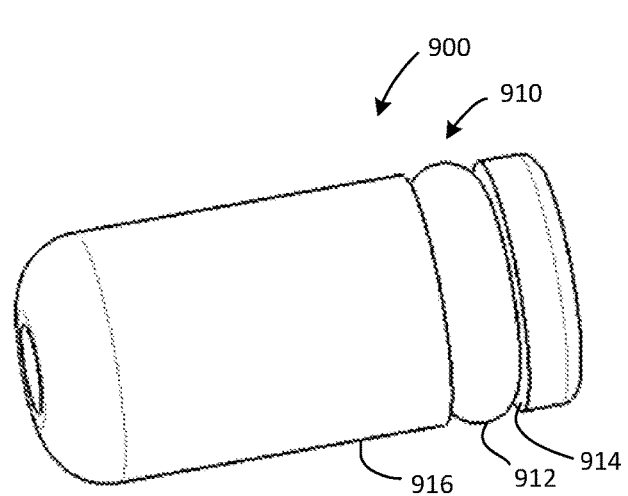
FIG. 9A is a perspective view of a guide bushing with a resilient member, according to one embodiment.

FIG. 9A shows an embodiment of a guide bushing 900 that may generally be configured similarly to the guide bushing 160 of FIG. 3A. However, the guide bushing 900 may have a resilient member 910 with a resilient member outer surface 912. The resilient member 910 may be engaged in a circumferential groove 914 in an exterior surface 916 of the guide bushing 900. The resilient member outer surface 912 may be sized to have a light interference fit with the trephine body inner surface 134 of the trephine body 120. This light interference fit, as provided by the resilient member 910, may provide relatively predictable resistance to sliding motion between the guide bushing 900 and the trephine body inner surface 134, facilitating proximal retraction of the guide bushing 900 into the trephine body inner chamber 136 to receive bone and/or cartilage fragments. Additionally or alternatively, the resilient member 910 may facilitate distal motion of the guide bushing 900 within the trephine body inner chamber 136 to eject the bone and/or cartilage fragments.

Figure 9B:
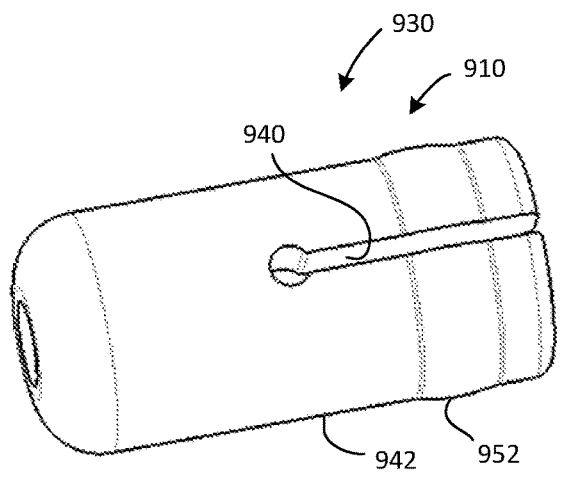
FIG. 9B is a perspective view of a guide bushing with longitudinal slots, according to one embodiment.

FIG. 9B shows an alternative embodiment of a guide bushing 930 having longitudinal slots 940 formed in a guide bushing outer surface 942 of the guide bushing 930. The longitudinal slots 940 may provide resiliency in a guide body proximal end 952 of the guide bushing 930, providing a light interference fit between the guide bushing outer surface 942 and the trephine body inner surface 134. Only one of the longitudinal slots 940 is visible in FIG. 9B; those skilled in the art will recognize that any number of longitudinal slots 940 may be used, including but not limited to one, two, three, four, five, six, seven, and eight. Like the guide bushing 900, the guide bushing 930 may provide predictable resistance to proximal and/or distal sliding motion of the guide bushing 930 within the trephine body inner chamber 136 of the trephine body 120.

Figure 9C:
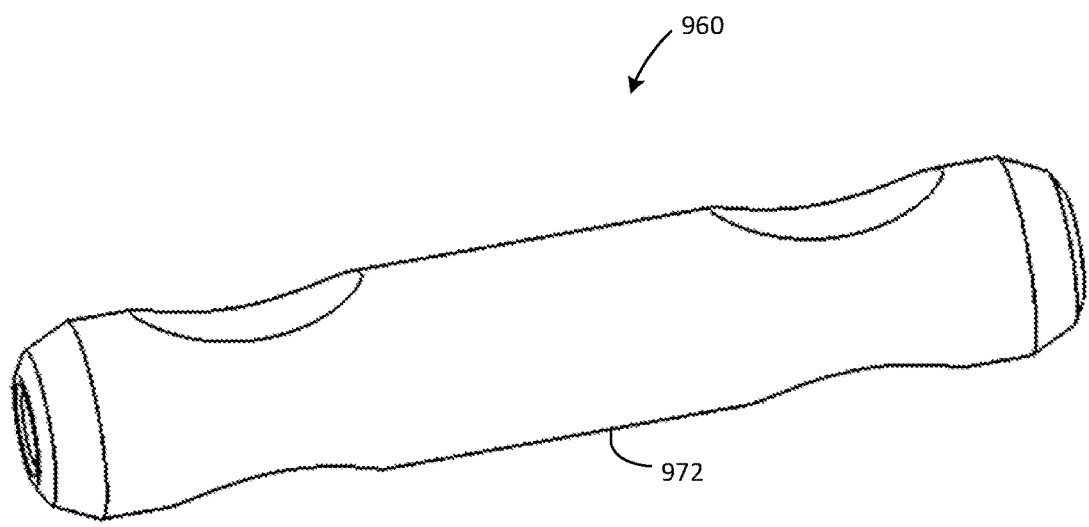
FIG. 9C is a perspective view of a guide bushing, according to another embodiment.

FIG. 9C shows yet another alternate embodiment of a guide bushing 960 having a guide bushing outer surface 972. The guide bushing 960 may be similar to the guide bushing 460 of FIG. 3B and may thus be designed for use with the trephine body 420. The guide bushing outer surface 972 of the guide bushing 960 may be adapted to have a close sliding clearance fit with the trephine body inner surface 434 of the trephine body 420. Like the guide bushing 900 and the guide bushing 930, the guide bushing 960 may provide predictable resistance to proximal and/or distal sliding motion of the guide bushing 960 within the trephine body inner chamber 436 of the trephine body 420.

Figure 10:
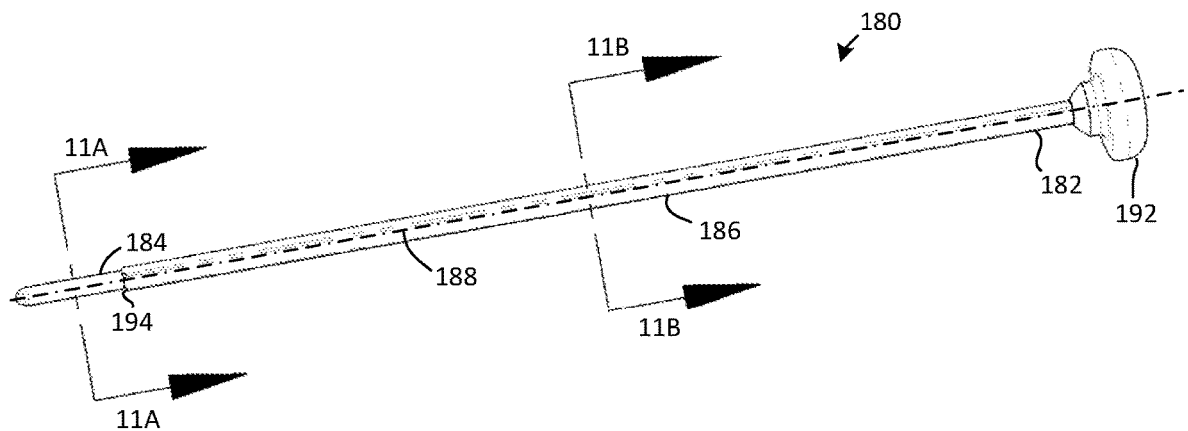
FIG. 10 is an enlarged view of the pushrod of FIG. 3A.
Figure 11A:
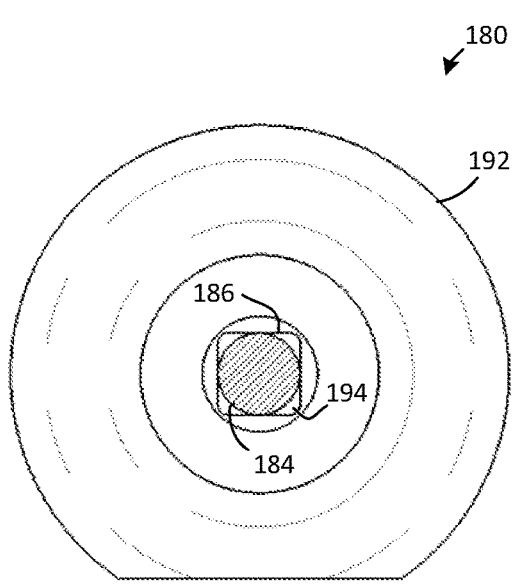
FIG. 11A is a section view of the pushrod distal end of the pushrod of FIG. 3A.
Figure 11B:
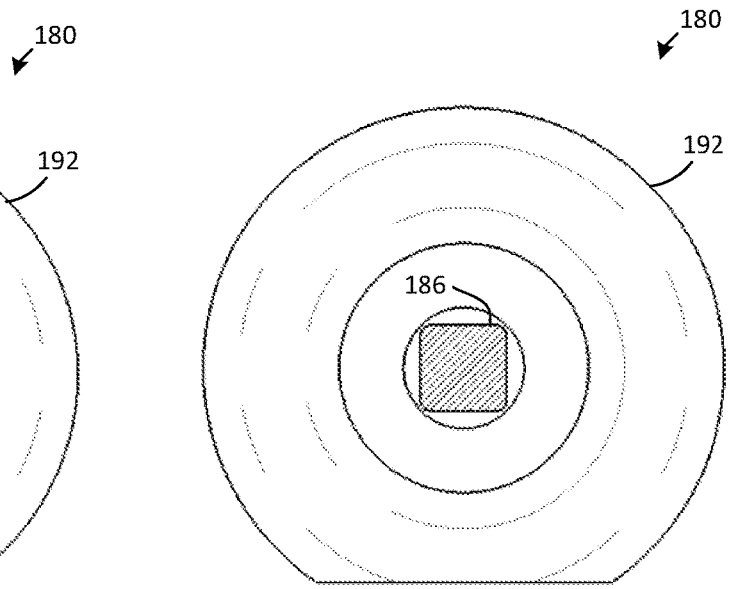
FIG. 11B is a section view of the pushrod intermediate portion of the pushrod of FIG. 3A.

FIG. 10 is an enlarged view of the pushrod 180 of FIG. 3A. FIG. 11A is a section view of the pushrod distal end 184 of the pushrod 180. FIG. 11B is a section view of the pushrod intermediate portion 186 of the pushrod 180.

As shown, the pushrod proximal end 182 and the pushrod intermediate portion 186 of the pushrod 180 may have a first cross sectional shape that is non-circular as shown in FIG. 11B. The pushrod distal end 184 of the pushrod 180 may have a second cross sectional shape that is circular as shown in FIG. 11A. The shoulder 194 of the pushrod 180 may be located at a transition between the first and second cross sections, and may be used to transmit a pushing force to the guide bushing proximal end 162 to urge the guide bushing 160 from the trephine body proximal end 122 toward the trephine body distal end 124. The first cross section may be sized to slidingly fit inside the drive shaft cannulation 156 of the drive shaft 140, and the second cross section may be sized to slidingly fit inside the guide bushing cannulation 176 of the guide bushing 160.

Figure 12A:
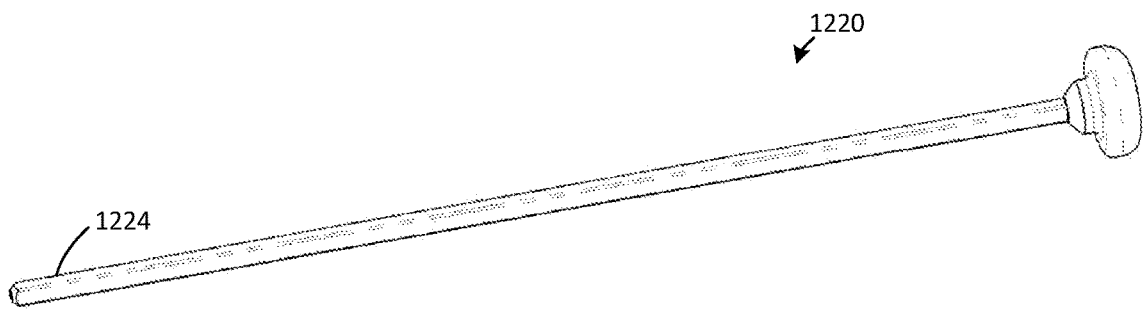
FIG. 12A is a perspective view of a pushrod according to one alternative embodiment.

FIG. 12A shows a perspective view of a pushrod 1220 according to one alternative embodiment. The pushrod 1220 may have a pushrod distal end 1224 that is adapted to transmit a pushing force to a guide bushing proximal end (for example, the guide bushing proximal end 162 of the guide bushing 160 of FIG. 3A) to urge the guide bushing 160 to move distally. There is no shoulder; thus, the pushrod distal end 1224 may simply abut the guide bushing proximal end 162 without residing in the guide bushing cannulation 176 of the guide bushing 160.

Figure 12B:
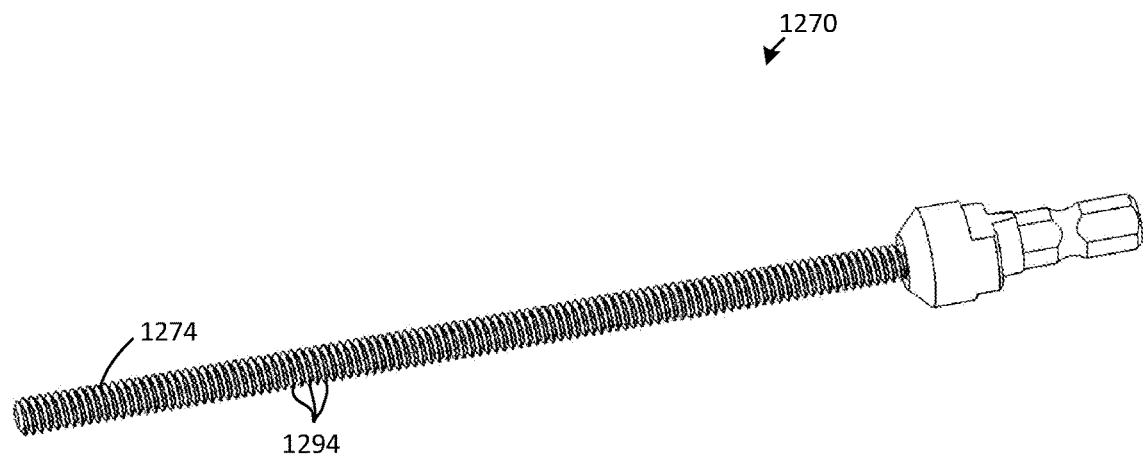
FIG. 12B is a perspective view of a pushrod according to another alternative embodiment.

FIG. 12B shows a perspective view of a pushrod 1270 according to another embodiment. The pushrod 1270 may be similar to the pushrod 480 of FIG. 3B, and may thus have threading 1294 adapted to engage an internal thread of a cannulation, such as the internal thread 700 of the drive shaft cannulation 456 shown in FIG. 7B. The pushrod 1270 may have a pushrod distal end 1274 that is adapted to transmit a pushing force to a guide bushing proximal end (for example, the guide bushing proximal end 462 of the guide bushing 460 of FIG. 3B) to urge the guide bushing 460 to move distally from the trephine body proximal end 422 toward the trephine body distal end 424.

Figure 13:
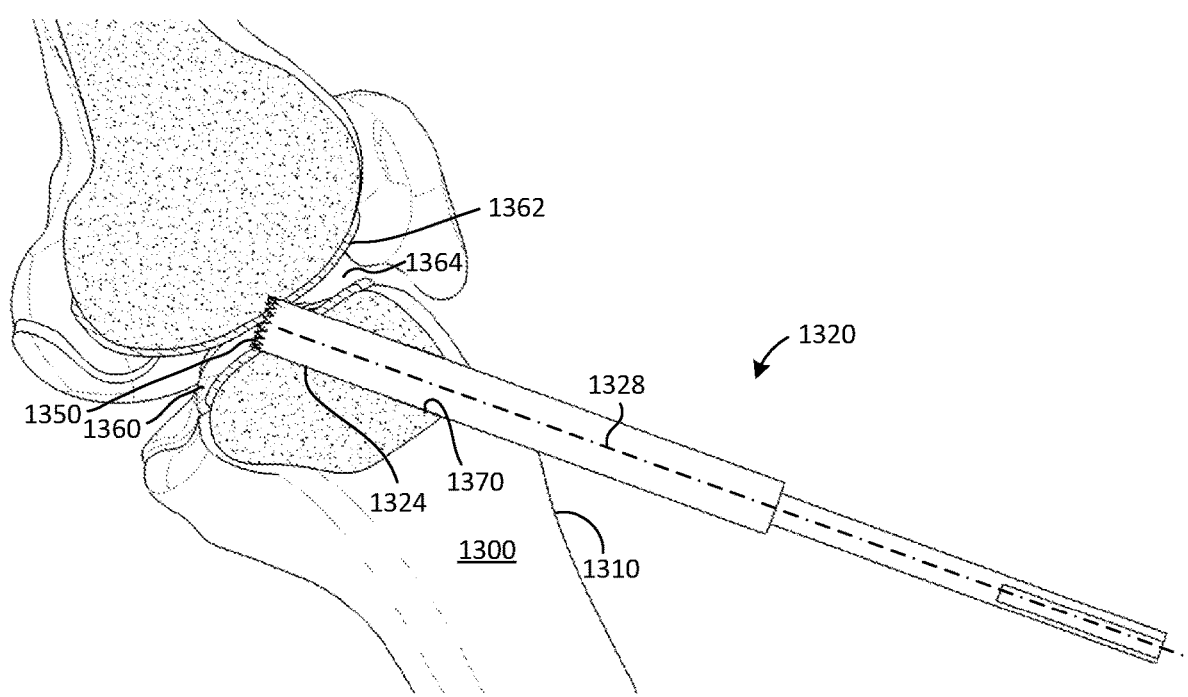
FIG. 13 is a perspective view of a prior art trephine positioned adjacent to a bone surface near an articular joint.

FIG. 13 is a perspective view of a prior art trephine 1320 positioned adjacent to a bone surface 1310 near an articular joint. The prior art trephine 1320 has a longitudinal axis 1328 and a distal end 1324 with a toothed rim 1350 that is substantially perpendicular to the longitudinal axis 1328. The articular joint may include comprised of a first cartilage surface 1360, a second cartilage surface 1362, and a joint space 1364 therebetween. In arthroscopic surgery, the joint space 1364 may be very limited, typically with only a few millimeters separating the first cartilage surface 1360 from the second cartilage surface 1362. Using a trephine in arthroscopic surgery to create a tunnel 1370 through bone 1300 and in communication with the joint space 1364 may involve the use of an oblique approach to the first cartilage surface 1360 or the second cartilage surfaces 1362. Due to this oblique approach and due to the limited joint space 1364, the distal end 1324 of the prior art trephine 1320 where cutting teeth are located may enter the joint space 1364 in an angled position relative to the joint space 1364. This angled positioning of the distal end 1324 may pose significant risk of cutting into the second cartilage surface 1362 when the surgical intent is only to create the tunnel 1370 through the first cartilage surface 1360. For example, it may be desirous to form the tunnel 1370 to access a cartilage lesion on the first cartilage surface 1360, while preserving the second cartilage surface 1362 where healthy tissue should remain pristine.

The trephine 100, the trephine 400, or any of the alternatives referenced above, may be used according to a variety of methods to help address this problem. One exemplary method will be shown and described in connection with the trephine 100 of FIG. 3A, which may include the guidewire 110, the trephine body 120, the drive shaft 140, the guide bushing 160, and the pushrod 180 as described previously.

According to one exemplary method of forming a tunnel through tissue, the guidewire 110 may be drilled into a tissue having a tissue surface. Next, the guide bushing 160 may be positioned in the trephine body inner chamber 436 near the trephine body distal end 424. The guide bushing cannulation 176 and the drive shaft cannulation 156 may be sized for a close sliding fit with the guidewire 110. As the trephine body 120 advances into the tissue, the guide bushing 160 may remain in contact with the bone surface and may retract proximally into the trephine body inner chamber 136, and the inner chamber fills with tissue. Once the trephine body 120 is advanced to full cutting depth, the trephine body 120 may be withdrawn from the tissue with the resected tissue captured in the trephine body inner chamber 136. To expel the tissue from the trephine body inner chamber 136, the pushrod 180 may then be inserted into the drive shaft proximal end 142 through the drive shaft cannulation 156 so that the shoulder 194 contacts the guide bushing proximal end 162 to urge the guide bushing 160 and the captured tissue toward the trephine body distal end 124.

Figure 14A:
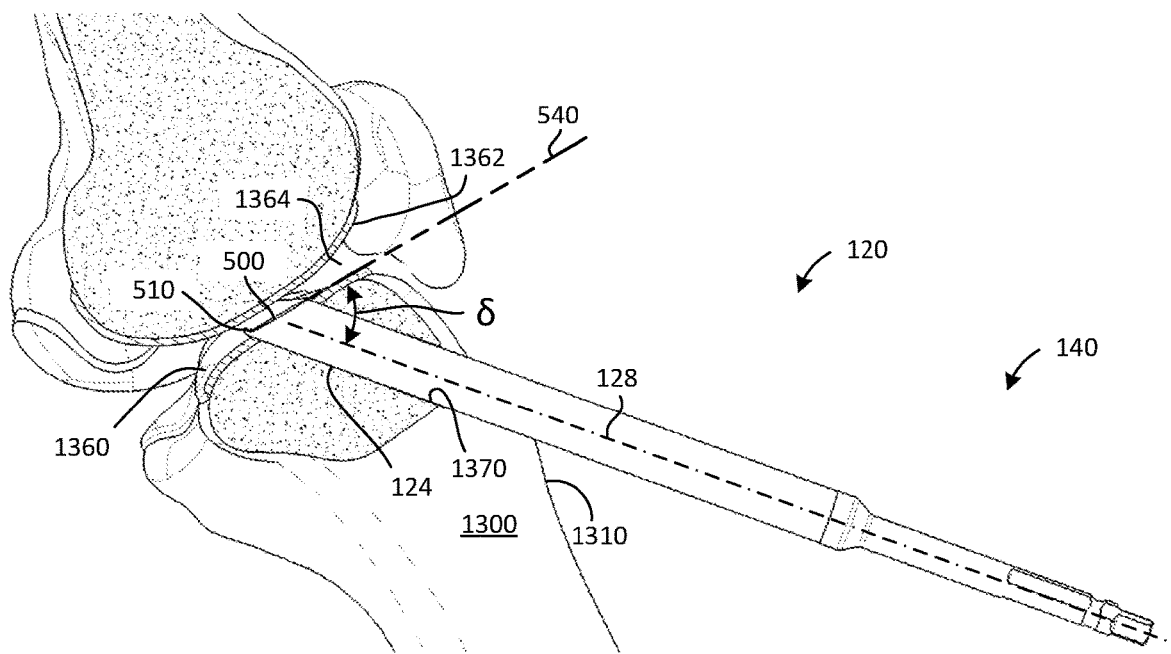
FIG. 14A is a perspective view of the trephine body of FIG. 3A, positioned near an articular joint with the trephine body in a first rotational position, according to one embodiment.
Figure 14B:
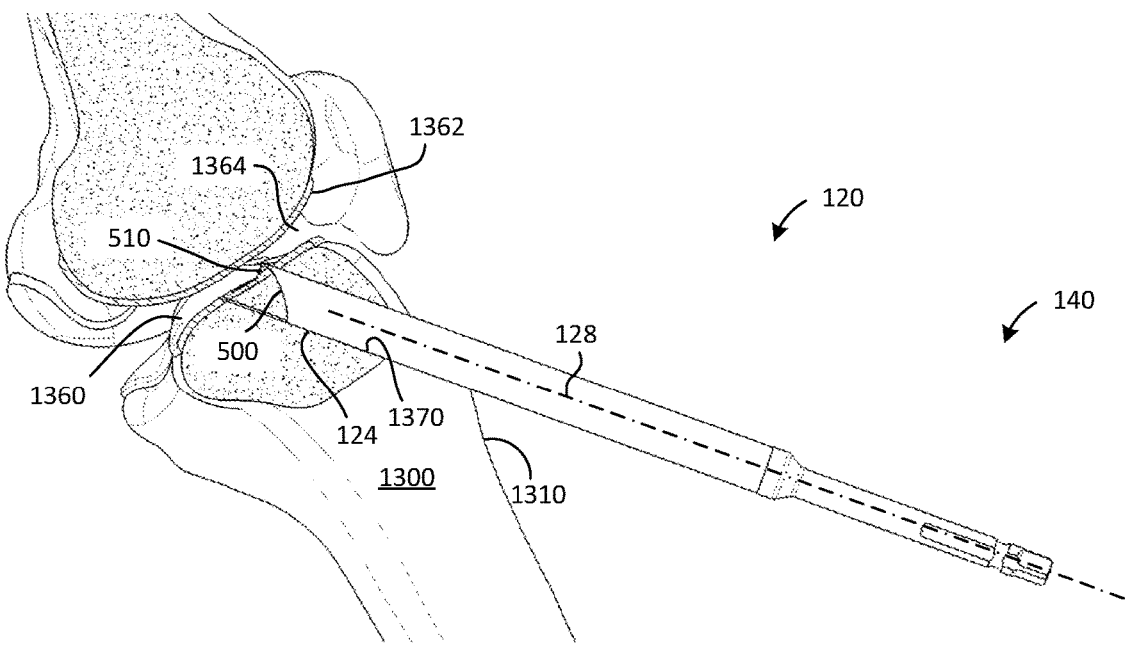
FIG. 14B is a perspective view of the trephine body of FIG. 3A near an articular joint, with the trephine body in a second rotational position, according to one embodiment.

FIGS. 14A and 14B show how the systems and methods of the present disclosure may be used to solve the problem with the prior art trephine described above. FIG. 14A is a perspective view of the trephine body 120 of FIG. 3A, positioned near an articular joint with the trephine body 120 in a first rotational position. As in FIG. 13, the joint may include a first cartilage surface 1360, a second cartilage surface 1362, and a joint space 1364 that separates the second cartilage surface 1362 from the first cartilage surface 1360. The trephine body 120 may again be inserted through the bone surface 1310 and used to form the tunnel 1370 such that the trephine body longitudinal axis 128 is non-perpendicular to the joint space 1364. Specifically, the trephine body longitudinal axis 128 may be oriented at an advancement angle δ of the trephine body 120 relative to the first cartilage surface 1360, the second cartilage surface 1362, and/or the joint space 1364.

As set forth above, the trephine body distal end 124 may have a trephine body distal rim 500 that lies in a plane 540 that is oriented non-perpendicular to the trephine body longitudinal axis 128. The angle of the plane 540 relative to a plane 542 perpendicular to the trephine body longitudinal axis 128 (rim angle φ, as described above) may be selected to be generally parallel to the joint space when the trephine body distal end 124 extends into the joint space 1364 when the trephine body 120 is drilled from outside the bone 1300 into the joint space 1364 with an oblique approach, in the first orientation of the trephine body 120 shown in FIG. 14A.

FIG. 14B is a perspective view of the trephine body 120 of FIG. 3A near an articular joint, with the trephine body 120 in a second rotational position. FIG. 14B shows how the trephine body 120 can be translated along the trephine body longitudinal axis 128 simultaneously with rotation of the trephine body longitudinal axis 128 about the trephine body longitudinal axis 128 to ensure that the trephine body distal end 124 or the cutting tooth 510 does not encroach into the second cartilage surface 1362. Furthermore, the simultaneous translation and rotation of the trephine body 120 can further maintain the cutting tooth 510 within the envelope of the first cartilage surface 1360 and/or within the joint space 1364, ensuring that there is no collateral damage to the second cartilage surface 1362.

This simultaneous rotation and translation of the trephine body 120 may be accomplished in a variety of ways. According to one example, the surgeon may rotate the trephine body 120 by hand under visualization, for example, with an endoscopic camera system (not shown) within the joint space 1364, fluoroscopy, or any other imaging systems known in the art. The surgeon may watch for the cutting tooth 510 to pierce the first cartilage surface 1360 and enter the joint space 1364, and when this happens, may begin to alternately withdraw the trephine body 120 proximally within the tunnel 1370, and insert the trephine body 120 distally further into the tunnel 1370, to ensure that the tunnel 1370 forms a complete intersection with the first cartilage surface 1360 without allowing the cutting tooth 510 or the trephine body distal rim 500 of the trephine body 120 to traverse the joint space 1364 and significantly damage the second cartilage surface 1362.

In the alternative, during cutting of a tunnel with the trephine body 120, as the cutting tooth 510 approaches the first cartilage surface 1360, operation of the trephine body 120 can be changed from a circumferential cutting motion, typically achieved with a power tool, to a linear cutting motion using hand control. In this case, the power tool may be disconnected from the trephine body 120, and a handle (not shown) may be attached to the trephine body 120. The surgeon may now gently advance the trephine body 120 with light mallet taps, in a direction parallel to the trephine body longitudinal axis 128, through the first cartilage surface 1360 while maintaining the plane 540 aligned with the joint space 1364. In this example, the first cutting face 222 and/or the second cutting face 224, which are adapted to cut in the circumferential directions (the clockwise direction 532 and the counterclockwise direction 534, respectively), may efficiently cut the bone while the rim cutting surface 250, which is adapted to cut in response to motion along the trephine body longitudinal axis 128, efficiently cuts through the first cartilage surface 1360.

In other alternative embodiments, a specialized driver (not shown) may be used, and may be designed to alternately move the trephine body 120 proximally and distally along the trephine body longitudinal axis 128, as described above, with the displacement needed to complete formation of the tunnel 1370 through the first cartilage surface 1360 without significantly damaging the second cartilage surface 1362. Such a driver may be driven manually and/or via motor, and may optionally be inactive as the proximal portion of the tunnel 1370 is formed, and then engaged as the cutting tooth 510 pierces any part of the first cartilage surface 1360.

Figure 15:
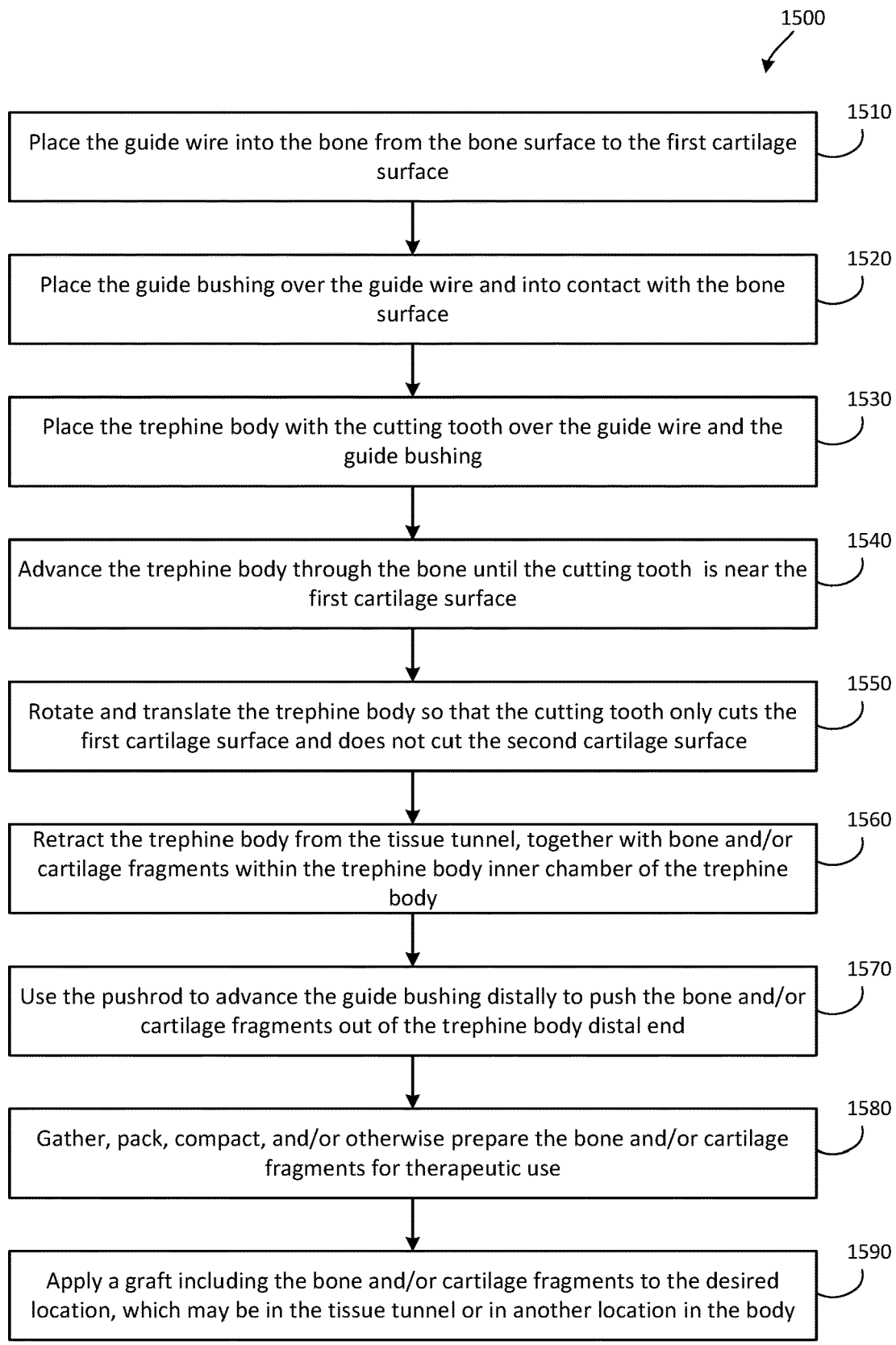
FIG. 15 is a flow chart showing a method of cutting bone and/or cartilage with the trephine of FIG. 3B, according to one embodiment.

FIG. 15 is a flow chart showing a method 1500 of cutting bone and/or cartilage with the trephine 100 of FIG. 3B, according to one embodiment. Those of skill in the art will recognize that the method 1500 may also be used in connection with the trephine 400 of FIG. 3A, or with other trephines that would be envisioned by a person skilled in the art with the aid of the present disclosure. Further, the trephine 100, the trephine 400, and other alternative trephines within the scope of this disclosure may be used with other methods besides the method 1500.

In a step 1510, the surgeon may place the guidewire 110 into the bone 1300 from the bone surface 1310 to the first cartilage surface 1360. In a step 1520, the surgeon may place the guide bushing 160 over the guidewire 110 and into contact with the bone surface 1310. In a step 1530, the surgeon may place the trephine body 120 with the cutting tooth 210 over the guidewire 110 and the guide bushing 160. In a step 1540, the surgeon may advance the trephine body 120 through the bone 1300 until the cutting tooth 210 is near the first cartilage surface 1360.

Then, in a step 1550, the surgeon may simultaneously rotate and translate the trephine body 120 so that the cutting tooth 510 only cuts the first cartilage surface 1360 and does not cut the second cartilage surface 1362. In a step 1560, the surgeon may retract the trephine body 120 from the tunnel 1370, together with bone and/or cartilage fragments within the trephine body inner chamber 136 of the trephine body 120. In a step 1570, the surgeon may use the pushrod 180 to advance the guide bushing 160 distally to push the bone and/or cartilage fragments out of the trephine body distal end 124.

In a step 1580, the surgeon may gather, pack, compact, and/or otherwise prepare the bone and/or cartilage fragments for therapeutic use. In a step 1590, the surgeon may apply a graft including the bone and/or cartilage fragments to the desired location, which may be in the tunnel 1370 or in another location in the body.

As mentioned previously, many variations to the foregoing systems and methods would be envisioned by a person skilled in the art, with the aid of the present disclosure. According to one alternative embodiment, a trephine body may have a distal rim that faces outward, rather than inward as in the embodiments shown and described previously. This embodiment will be shown and described in connection with FIGS. 16A, 16B, 17A, and 17B, as follows.

Figures 16A, 16B:
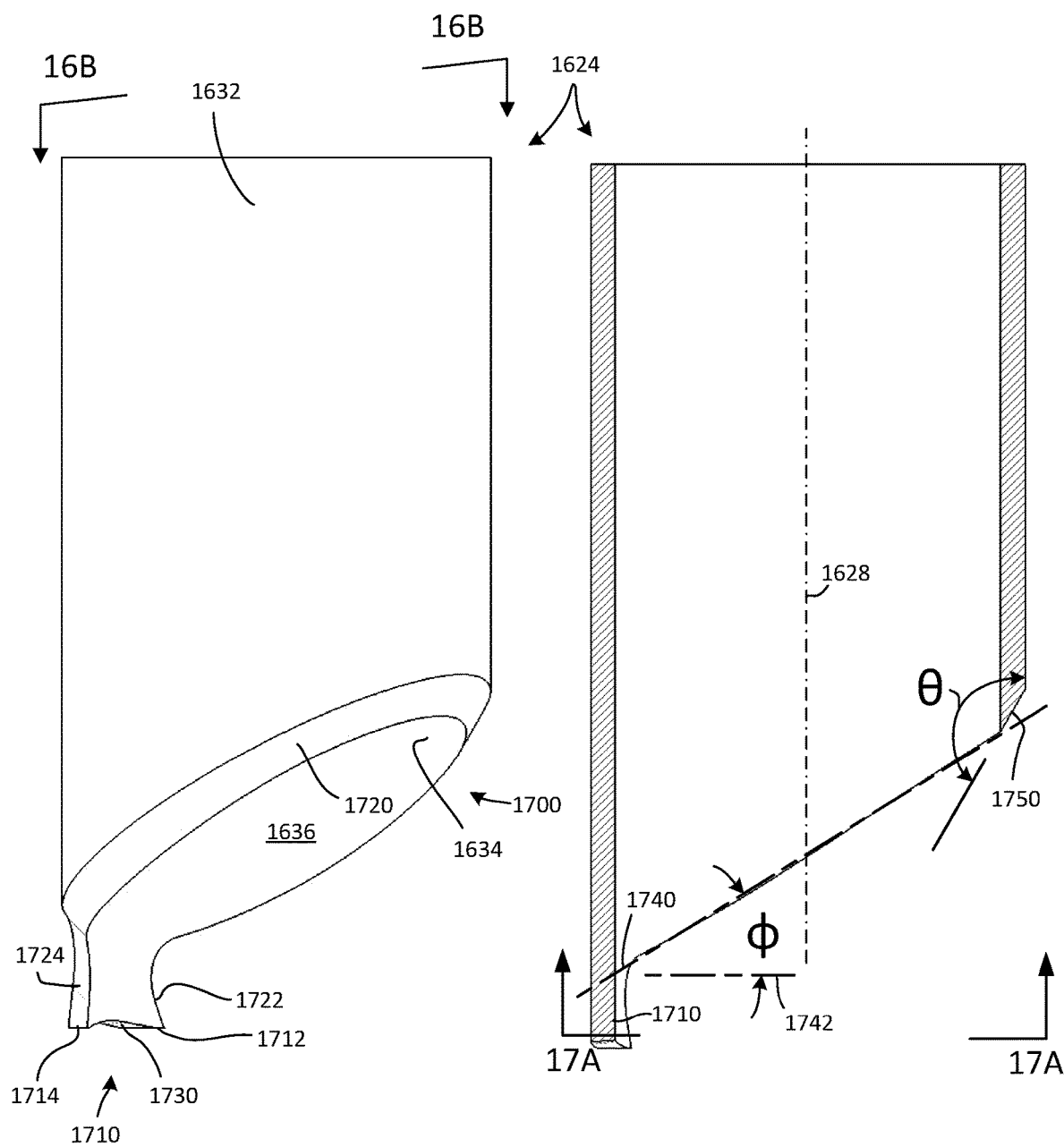
FIG. 16A is a side view of a trephine body distal end of a trephine body according to one alternative embodiment, at a first rotational position relative to a trephine body longitudinal axis.
FIG. 16B is a section view of the trephine body distal end of FIG. 16A, along the corresponding lines shown in FIG. 16A.
Figure 17A:
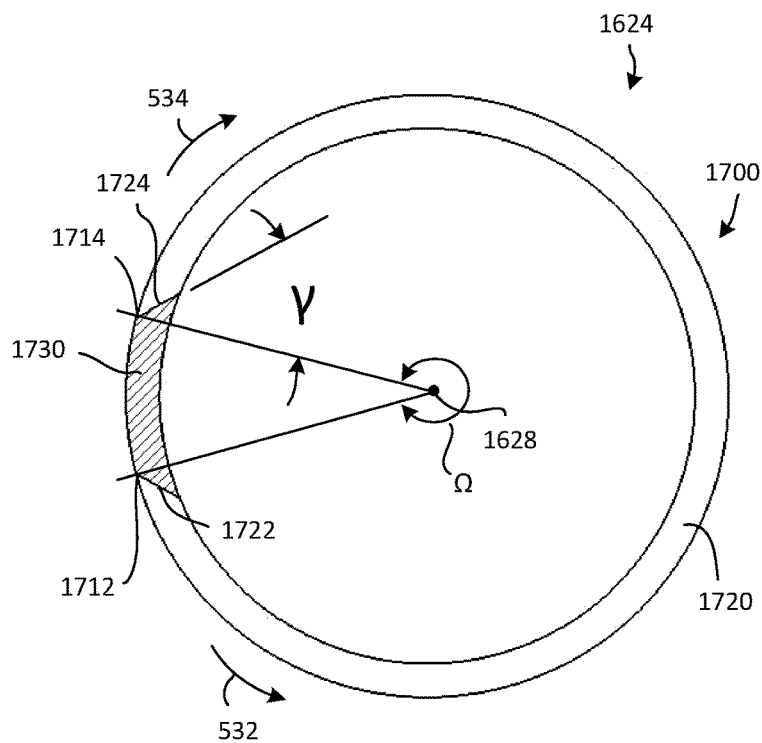
FIG. 17A is a section view of the trephine body of FIG. 16A, along the corresponding lines shown in FIG. 16B.
Figure 17B:
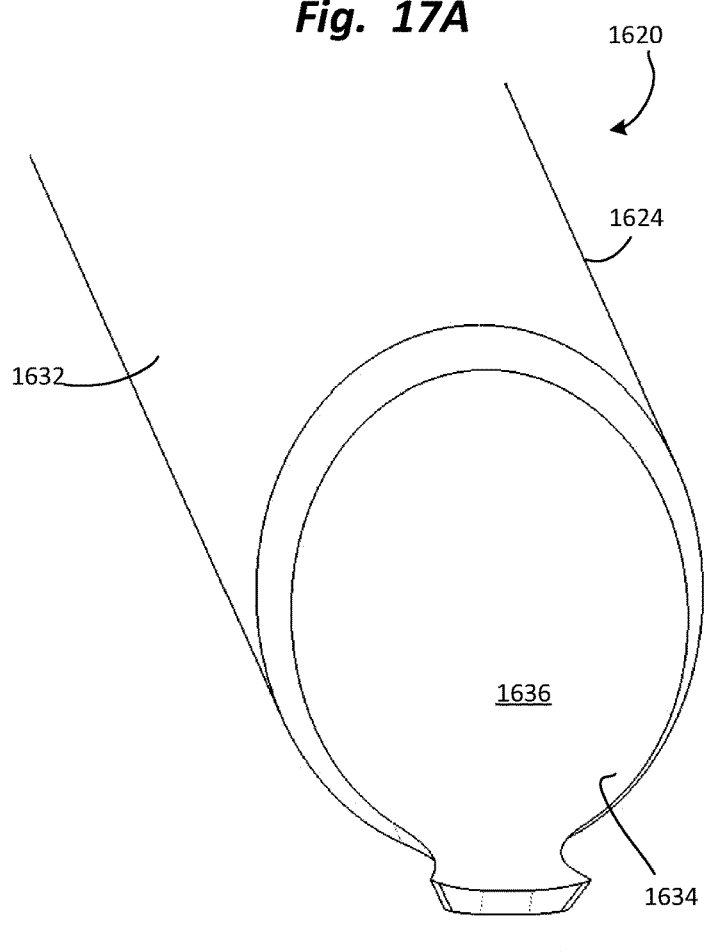
FIG. 17B is an enlarged, perspective view of the trephine body distal end of the trephine body of FIG. 16A.

FIG. 16A is a side view of a trephine body distal end 1624 of a trephine body 1620 according to one alternative embodiment, at a first rotational position relative to a trephine body longitudinal axis 1628. FIG. 16B is a section view of the trephine body distal end 1624, along the corresponding lines shown in FIG. 16A. FIG. 17A is a section view of the trephine body 1620, along the corresponding lines shown in FIG. 16B. FIG. 17B is an enlarged, perspective view of the trephine body distal end 1624 of the trephine body 1620 of FIG. 16A.

As shown in FIG. 16A, the trephine body 1620 may have a generally tubular shape with a trephine body outer surface 1632, a trephine body inner surface 1634. The generally tubular shape may define a trephine body inner chamber 1636. The trephine body distal end 1624 of the trephine body 1620 may have a trephine body distal rim 1700. Like the trephine body distal rim 500, the trephine body distal rim 1700 may cut bone and/or cartilage to form the tunnel. The trephine body distal rim 1700 may be oriented outward to direct fragments of removed bone and/or cartilage toward the trephine body outer surface 1632, removing them from the cutting area.

As shown in FIG. 16B, the trephine body distal rim 1700 may extend in the circumferential direction and lies substantially in a plane 1740. The plane 1740 may be oriented at a rim angle $\phi$ such that the plane 1740 is non-perpendicular to the trephine body longitudinal axis 1628, and is thus nonparallel to a plane 1742 perpendicular to the trephine body longitudinal axis 1628. The rim angle $\phi$ is the angle between the plane 1740 and the plane 1742. As in the previous embodiment, the rim angle $\phi$ may be greater than 0°, and may fall within any of the ranges or angles set forth in the discussion of previous embodiments.

A cutting tooth 1710 may extend distally from the trephine body distal rim 1700. More specifically, the trephine body distal rim 1700 may have a proximal portion and a distal portion (for example, with reference to FIG. 16B, the portions of the trephine body distal rim 1700 on the right and left sides of the trephine body longitudinal axis 1628, respectively). The cutting tooth 1710 may be integrally formed with the trephine body distal rim 1700, or may be formed separately and attached thereto by any method known in the art, including but not limited to mechanical fastening, chemical bonding, adhesive bonding, welding, and the like. As shown, only a single cutting tooth (e.g., the cutting tooth 1710) may be present; the cutting tooth 1710 may be configured to cut the bone and/or cartilage independently of any other teeth or other cutting implements. Thus, in the embodiment shown, no other cutting feature besides the cutting tooth 1710 may extend distally beyond the trephine body distal rim 1700.

Thus, as shown in FIG. 17A, the trephine body distal rim 1700 may have an uninterrupted portion 1720 that traverses an angle $\Omega$ of at least 180° of the circumference of the trephine body distal rim 1700. The angle $\Omega$ may fall within any of the ranges or angles set forth in the discussion of previous embodiments.

The cutting tooth 1710 may have a first distal tip 1712 and a second distal tip 1714. The first distal tip 1712 may connect to the trephine body distal rim 1700 via a first cutting face 1722, and the second distal tip 1714 may connect to the trephine body distal rim 1700 via a second cutting face 1724. The first distal tip 1712 may be connected to the second distal tip 1714 by a distal surface 1730. The distal surface 1730 may have a concave shape such that the first distal tip 1712 and/or the second distal tip 1714 are acutely angled. The first cutting face 1722 and/or the second cutting face 1724 may be tapered such that they approach each other along the proximal direction to further accentuate the acute angulation of the first distal tip 1712 and/or the second distal tip 1714. In other words, the first cutting face 1722 and/or the second cutting face 1724 may be angled to face slightly toward the trephine body distal rim 1700. This angulation may cause the cutting tooth 1710 to be wider at its distal end than at its proximal end. The angulation of the first cutting face 1722 and/or the second cutting face 1724 may cause the first cutting face 1722 and/or the second cutting face 1724 to have a positive longitudinal rake angle α (not demarcated) under clockwise rotation and/or counterclockwise rotation, respectively. The longitudinal rake angle Ω may fall within any of the ranges or angles set forth in the discussion of previous embodiments.

The first distal tip 1712 and the second distal tip 1714 may be spaced apart in a circumferential direction such that the first distal tip 1712 and the first cutting face 1722 are adapted to efficiently cut in the clockwise direction 532, and the second distal tip 1714 and the second cutting face 1724 are adapted to efficiently cut in the counterclockwise direction 534.

As shown in FIG. 16B, the trephine body distal rim 1700 may have a rim cutting surface 1750 on the uninterrupted portion 1720. The rim cutting surface 1750 may be adapted for cutting in a direction that is parallel to the trephine body longitudinal axis 1628. The rim cutting surface 1750 may have a bevel angle θ as shown in FIG. 16B. As the trephine body 1620 cuts and traverses deeper into the tissue, the bevel angle θ may provide for efficient cutting in a direction that is parallel to the trephine body longitudinal axis 1628. Thus, the first cutting face 1722, the second cutting face 1724, and/or the distal surface 1730 may generally cut tissue in response to rotation of the trephine body longitudinal axis 1628, while the rim cutting surface 1750 cuts the tissue in response to axial advancement of the trephine body longitudinal axis 1628 into the tissue.

The bevel angle θ may provide for efficient cutting in response to this axial motion, and/or efficient direction of bone and/or cartilage fragments out to the exterior of the trephine body 1620. The bevel angle θ may be the angle of the rim cutting surface 1750 of the trephine body distal rim 1700 at a position diametrically opposed to that of the cutting tooth 1710. The rim cutting surface 1750 may have a variable angle or a constant angle, relative to the trephine body longitudinal axis 1628, with the bevel angle θ as the relative angle at the location opposite the cutting tooth 1710. More particularly, in some embodiments, the bevel angle θ may be the same across substantially the entirety of the trephine body distal rim 1700, with the possible exception of the region of the trephine body distal rim 1700 that is adjacent to the cutting tooth 1710. This may provide for more consistent cutting of bone and/or cartilage in response to axial motion of the trephine body 1620 into the tissue.

In some embodiments, the bevel angle θ may be within the range of 100° to 170°. More precisely, in some embodiments, the bevel angle θ may be within the range of 105° to 160°. Yet more precisely, in some embodiments, the bevel angle θ may be within the range of 110° to 150°. Still more precisely, in some embodiments, the bevel angle θ may be within the range of 115° to 140°. Even more precisely, in some embodiments, the bevel angle θ may be within the range of 120° to 135°.

With further reference to FIG. 17A, each of the first cutting face 1722 and the second cutting face 1724 may be angled toward the trephine body outer surface 1632 such that they effectively remove bone and/or cartilage to form the tunnel, and so that they direct removed bone and/or cartilage outward and along the exterior of the trephine body 1620. More specifically, the first cutting face 1722 and the second cutting face 1724 may each be oriented at a radial rake angle γ, as shown. The radial rake angle γ may be the angle of the first cutting face 1722 and/or the second cutting face 1724 relative to a radial line passing from the trephine body longitudinal axis 1628, passing through the first cutting face 1722 or the second cutting face 1724, respectively, as shown in FIG. 17A. In this embodiment, the radial rake angle γ may be negative, reflecting the outward orientation of the first cutting face 1722 and the second cutting face 1724.

In some embodiments, the radial rake angle γ may be within the range of 0° to −80°. More precisely, in some embodiments, the radial rake angle γ may be within the range of −10° to −70°. Yet more precisely, in some embodiments, the radial rake angle γ may be within the range of −20° to −60°. Still more precisely, in some embodiments, the radial rake angle γ may be within the range of −30° to −50°. Even more precisely, in some embodiments, the radial rake angle γ may be within the range of −35° to −45°. Still further, in some embodiments, the radial rake angle γ may be about −40°. Optionally, the radial rake angle γ may be the same for the first cutting face 1722 and the second cutting face 1724 to facilitate efficient cutting in the clockwise direction 532 and the counterclockwise direction 534, respectively.

In use, the trephine body 1620 may be similar to the trephine body 420, except that bone and/or cartilage fragments are directed out to the exterior of the trephine body 1620, rather than into the trephine body inner chamber 1636. Known methods may be used for removing these bone and/or cartilage fragments from the bone tunnel, independently from withdrawal of the trephine body 1620 if needed.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment. Features and/or method steps of the various different embodiments set forth above may be combined together to yield new embodiments. The drawings are drawn to scale, but the shapes and dimensions shown in the drawings are merely exemplary. Various features and/or dimensions may be modified within the understanding of a person of ordinary skill in the art with the aid of the present disclosure.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

As used herein, the term "proximal" means a location relatively closer to a user (i.e., a surgeon) when the user is installing the implant. The term "distal" means a location relatively further from the user. For example, when a user installs a bone screw into a material with a driver, the end of the bone screw engaged with the driver is the proximal end, and the tip of the bone screw that first engages the material is the distal end. The term "cannulated" means having a central bore extending along a longitudinal axis of a part between a proximal end and a distal end of the part.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. As defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. A trephine for forming a tunnel through bone and/or cartilage, the trephine comprising:
   a trephine body having a generally tubular shape centered on a trephine body longitudinal axis, the trephine body comprising a trephine body proximal end and a trephine body distal end that defines a trephine body distal rim; and
   a drive shaft coupled to or configured to be coupled to the trephine body proximal end such that the drive shaft receives torque and transmits the torque to the trephine body;
   wherein an entirety of the trephine body distal rim lies substantially in a single plane that is non-perpendicular to the trephine body longitudinal axis;
   wherein the trephine body distal rim comprises an uninterrupted portion that traverses at least 180° of a circumference of the trephine body distal rim.

2. The trephine of claim 1, wherein the plane is oriented at a rim angle, relative to a second plane perpendicular to the trephine body longitudinal axis; and
   the rim angle is between 10° and 80°.

3. The trephine of claim 1, further comprising a cutting tooth extending distally from the trephine body distal rim.

4. The trephine of claim 3, wherein:
   the cutting tooth comprises:
      a first distal tip;
      a first cutting face extending from the trephine body distal rim to the first distal tip; and
   the first cutting face is configured to act as a leading cutting face such that the trephine is adapted to cut the bone and/or cartilage while rotating clockwise.

5. The trephine of claim 4, wherein:
   the cutting tooth further comprises:
      a second distal tip;
      a second cutting face extending from the trephine body distal rim to the second distal tip; and
   the second cutting face is configured to act as a leading cutting face such that the trephine is adapted to cut the bone and/or cartilage while rotating counterclockwise.

6. The trephine of claim 1, further comprising a guide bushing comprising a guide bushing cannulation;
   wherein:
      the drive shaft comprises a drive shaft cannulation;
      the drive shaft cannulation and the guide bushing cannulation are configured to receive a guidewire such that the drive shaft and the guide bushing are rotatable about the guidewire; and
      the guide bushing is slidably receivable within the generally tubular shape such that the guide bushing is movable along the trephine body longitudinal axis as the trephine body forms the tunnel.

7. The trephine of claim 6, further comprising a pushrod comprising:
   a proximal end configured to be slidably received or threaded into engagement within the drive shaft cannulation; and
   a distal end configured to push against the guide bushing to urge the guide bushing to move distally within the generally tubular shape.

8. A trephine for forming a tunnel through bone and/or cartilage, the trephine comprising:
   a trephine body having a generally tubular shape centered on a trephine body longitudinal axis, the trephine body comprising a trephine body proximal end and a trephine body distal end that defines a trephine body distal rim;
   a cutting tooth extending distally from the trephine body distal rim; and
   a drive shaft coupled to or configured to be coupled to the trephine body proximal end such that the drive shaft receives torque and transmits the torque to the trephine body;
   wherein an entirety of the trephine body distal rim is non-perpendicular to the trephine body longitudinal axis and is not interrupted by any protrusion other than the cutting tooth;
   wherein the trephine body distal rim comprises an uninterrupted portion that traverses at least 180° of a circumference of the trephine body distal rim.

9. The trephine of claim 8, wherein the trephine body distal rim lies substantially within a plane.

10. The trephine of claim 9, wherein:
    the plane is oriented at a rim angle, relative to a second plane perpendicular to the trephine body longitudinal axis; and
    the rim angle is between 10° and 80°.

11. The trephine of claim 8, wherein the uninterrupted portion traverses at least 270° of the circumference of the trephine body distal rim.

12. The trephine of claim 8, wherein:
    the cutting tooth comprises:
       a first distal tip; and
       a first cutting face extending from the trephine body distal rim to the first distal tip;

wherein the first cutting face is oriented at a longitudinal rake angle, relative to the trephine body longitudinal axis, that is greater than 0°.

13. The trephine of claim 8, wherein:
the cutting tooth comprises:
   a first distal tip;
   a second distal tip;
   a first cutting face extending from the trephine body distal rim to the first distal tip; and
   a second cutting face extending from the trephine body distal rim to the second distal tip; and
the first cutting face and the second cutting face are each configured to act as a leading cutting face such that the trephine is adapted to cut the bone and/or cartilage while rotating either clockwise or counterclockwise.

14. A trephine for forming a tunnel through bone and/or cartilage, the trephine comprising:
a trephine body having a generally tubular shape centered on a trephine body longitudinal axis, the trephine body comprising a trephine body proximal end and a trephine body distal end that defines a trephine body distal rim comprising:
   a proximal portion; and
   a distal portion extending distally of the proximal portion;
a cutting tooth extending distally from the distal portion, the cutting tooth comprising:
   a cutting tooth proximal end adjacent to the distal portion; and
   a cutting tooth distal end displaced distally from the distal portion; and
a drive shaft coupled to or configured to be coupled to the trephine body proximal end such that the drive shaft receives torque and transmits the torque to the trephine body;
wherein the cutting tooth distal end is wider than the cutting tooth proximal end;

wherein:
the cutting tooth comprises:
   a first distal tip; and
   a first cutting face extending from the trephine body distal rim to the first distal tip; and
the first cutting face is oriented at a longitudinal rake angle, relative to the trephine body longitudinal axis, that is greater than 0°.

15. The trephine of claim 14, wherein the trephine body distal rim lies substantially within a plane that is non-perpendicular to the trephine body longitudinal axis.

16. The trephine of claim 15, wherein:
the plane is oriented at a rim angle, relative to a second plane perpendicular to the trephine body longitudinal axis; and
the rim angle is between 10° and 80°.

17. The trephine of claim 14, wherein the trephine body distal rim comprises an uninterrupted portion that traverses at least 180° of a circumference of the trephine body distal rim.

18. The trephine of claim 14, wherein:
the cutting tooth distal end further comprises:
   a second distal tip displaced circumferentially from the first distal tip; and
the first distal tip is connected to the second distal tip by a distal surface having a concave shape.

19. The trephine of claim 14, wherein:
the cutting tooth further comprises:
   a second distal tip displaced circumferentially from the first distal tip on the cutting tooth distal end;
   a second cutting face extending from the trephine body distal rim to the second distal tip; and
the first cutting face and the second cutting face are each configured to act as a leading cutting face such that the trephine is adapted to cut the bone and/or cartilage while rotating either clockwise or counterclockwise.

* * * * *